(12) United States Patent
Kimchi et al.

(10) Patent No.: US 8,436,145 B2
(45) Date of Patent: *May 7, 2013

(54) COMPOSITIONS AND METHODS FOR DIAGNOSING AND TREATING CANCER AND NEURODEGENERATIVE DISEASES RELATED TO BECLIN-1

(75) Inventors: Adi Kimchi, Rehovot (IL); Einat Zalckvar, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,271

(22) Filed: Jun. 3, 2011

(65) Prior Publication Data

US 2011/0300559 A1 Dec. 8, 2011

Related U.S. Application Data

(63) Continuation of application No. PCT/IL2009/001150, filed on Dec. 6, 2009.

(60) Provisional application No. 61/175,803, filed on May 6, 2009, provisional application No. 61/119,745, filed on Dec. 4, 2008.

(51) Int. Cl.
*C07K 16/00* (2006.01)

(52) U.S. Cl.
USPC .................. 530/387.1; 530/388.1; 530/389.1

(58) Field of Classification Search .................. None
See application file for complete search history.

(56) References Cited

U.S. PATENT DOCUMENTS

| | | | |
|---|---|---|---|
| 4,376,110 A | 3/1983 | David | |
| 5,858,669 A | 1/1999 | Levine | |
| 6,432,914 B1 | 8/2002 | Levine | |
| 6,703,212 B1 | 3/2004 | Janoshazi | |
| 6,962,793 B2 | 11/2005 | Diamandis | |
| 7,348,149 B2 | 3/2008 | Feder | |
| 2005/0276809 A1 | 12/2005 | Baehrecke | |
| 2006/0019256 A1 | 1/2006 | Clarke | |
| 2007/0280935 A1* | 12/2007 | Bohrmann et al. | 424/133.1 |
| 2009/0099072 A1 | 4/2009 | Geneste | |
| 2011/0229905 A1 | 9/2011 | Kimchi | |
| 2011/0301093 A1 | 12/2011 | Kimchi | |

FOREIGN PATENT DOCUMENTS

| | | |
|---|---|---|
| CN | 1635144 | 7/2005 |
| WO | 01/40261 | 6/2001 |

OTHER PUBLICATIONS

Zalckvar et al, EMBO reports 10:285-292, published online Jan. 2009.*
Balduini, Walter et al., "Autophagy in hypoxia-ischemia induced brain injury: evidence and speculations", Autophagy, 5(2):221-223 (2009).
Beer, Ilan et al., "Improving large-scale proteomics by clustering of mass spectrometry data", Proteomics, 4(4):950-960 (2004).
Berry, Deborah L. and Baehrecke, Eric H., "Growth arrest and autophagy are required for salivary gland cell degradation in *Drosophila*", Cell, 131(6):1137-1148 (2007).
Bialik, Shani and Kimchi, Adi, "Autophagy and tumor suppression: recent advances in understanding the link between autophagic cell death pathways and tumor development", Adv Exp Med Biol, 615:177-200 (2008).
Buskens, Christianne et al., "Adenocarcinomas of the gastro-esophageal junction: A comparative study of the gastric cardia and esophagus with respect to cyclooxygenase-2 expression", Digestive Disease Week Abstracts and Itinnerary Planner 2003 Publishing ID:850 Abstract ID:101362 (2003).
Cherra, Salvatore J. III and Chu, Charleen T., "Autophagy in neuroprotection and neurodegeneration: A question of balance", Future Neurol, 3(3):309-323 (2008).
Cohen, Ofer et al., "DAP-kinase is a Ca2+/calmodulin-dependent, cytoskeletal-associated protein kinase, with cell death-inducing functions that depend on its catalytic activity", EMBO J, 16(5):998-1008 (1997).
Daniel, F. et al., "Beclin 1 mRNA strongly correlates with Bcl-XLmRNA expression in human hepatocellular carcinoma", Cancer Invest, 25(4):226-231 (2007).
Dermer, Gerald B., "Another Anniversary for the war on Cancer", Bio/Technology, 12:320 (1994).
Ding, Zhen-Bin et al., "Association of autophagy defect with a malignant phenotype and poor prognosis of hepatocellular carcinoma", Cancer Resm 68(22):9167-9175 (2008).
Drexler, Hans G., "Recent results on the biology of Hodgkin and Reed-Sternberg cells. II. Continuous cell lines", Leuk Lymphoma, 9(1-2):1-25 (1993).
Duan, Zhen-Ling et al., "Correlation of autophagy gene Beclin1 to tumorigenesis and development of epithelial ovarian cancer", Ai Zheng. 26(3):258-263 (English translation appeared in: Chinese Journal of Cancer 26(3):225-230) (2007).
Freshney Culture of animal cells, A manual of basic technique, Alan R. Liss Inc., 1983 New York p. 4.
Gozuacik, Devrim and Kimchi, Adi, "Autophagy and cell death", Curr Top Dev Biol, 78:217-245 (2007).
Kabeya, Yukiko et al., "LC3, a mammalian homologue of yeast Apg8p, is localized in autophagosome membranes after processing", EMBO J, 19(21):5720-5728 (2000).
Kaiser, Jocelyn, "Cancer. First pass at cancer genome reveals complex landscape", Science, 313(5792):1370 (2006).
Kohler, G. and Milstein, C., "Continuous cultures of fused cells secreting antibody of predefined specificity", Nature, 256(5517):495-497 (1975).
Koneri , Kenji et al., "Beclin 1 gene inhibits tumor growth in colon cancer cell lines", Anticancer Res, 27(3B):1453-1457 (2007).

(Continued)

*Primary Examiner* — Lei Yao
(74) *Attorney, Agent, or Firm* — Rodney J. Fuller; Booth Udall Fuller, PLC

(57) ABSTRACT

The present invention relates to antibodies specific for human Beclin-1 protein phosphorylated at position Thr 119 and uses thereof. In particular, these antibodies are useful in diagnosing diseases associated with impaired autophagy including cancer and neurodegenerative diseases. The invention further relates to human Beclin-1 mutated at position 119 with a phospho-mimicking residue and uses thereof for treating cancer and neurodegenerative diseases.

7 Claims, 13 Drawing Sheets

OTHER PUBLICATIONS

Levine, Beth and Kroemer, Guido, "Autophagy in the pathogenesis of disease", Cell, 132(1):27-42, (2008).
Liang, Xiao Huan et al., "Induction of autophagy and inhibition of tumorigenesis by beclin 1", Nature, 402(6762):672-676 (1999).
Maiuri, M. Chiara et al., "Functional and physical interaction between Bcl-X(L) and a BH3-like domain in Beclin-1", EMBO J, 26(10):2527-2539 (2007).
Martinez-Vicente, Marta and Cuervo, Ana Maria, "Autophagy and neurodegeneration: when the cleaning crew goes on strike", Lancet Neurol, 6(4):352-361 (2007).
Miracco, Clelia, "Protein and mRNA expression of autophagy gene Beclin 1 in human brain tumours", Int J Oncol, 30(2):429-436 (2007).
Niu, Hua et al., "Subversion of cellular autophagy by *Anaplasma phagocytophilum*", Cellular Microbiol, 10(3):593-605 (2008).
Oberstein, Adam et al., "Crystal structure of the Bcl-XL-Beclin 1 peptide complex: Beclin 1 is a novel BH3-only protein", J Biol Chem, 282(17):13123-13132 (2007).
Pattingre, Sophie et al., "Bcl-2 antiapoptotic proteins inhibit Beclin 1-dependent autophagy", Cell, 122(6):927-939 (2005).
Pickford, Fiona et al., "The autophagy-related protein beclin 1 shows reduced expression in early Alzheimer disease and regulates amyloid beta accumulation in mice", J Clin Invest, 118(6):2190-2199 (2008).
Pritzker, Kenneth P. H., "Cancer biomarkers: easier said than done", Clinical Chemistry, 48(8):1147-1150 (2002).
Shibata, Mamoru et al., "Regulation of intracellular accumulation of mutant Huntingtin by Beclin 1", J Biol Chem, 281(20):14474-14485 (2006).
Wang, Zan-Hong et al., "Expression and clinical significance of autophagy gene Beclin 1 in cervical squamous cell carcinoma", J Sichuan Univ Med Sci Edi.( Sichuan Da Xue Xue Bao Yi Xue Ban)37(6):860-863 (translated abstract) (2006).
Zalckvar, Einat et al., "DAP-kinase-mediated phosphorylation on the BH3 domain of beclin 1 promotes dissociation of beclin 1 from Bcl-XL and induction of autophagy", EMBO Rep, 10(3):285-292 (2009).
Zalckvar, Einat et al., "Phosphorylation of Beclin 1 by DAP-kinase promotes autophagy by weakening its interactions with Bcl-2 and Bcl-XL", Autophagy, 5(5):720-722 (2009).
Zellner, A. et al., "Disparity in expression of protein kinase C alpha in human glioma versus glioma-derived primary cell lines: therapeutic implications", Clin Cancer Res, 4(7):1797-1802 (1998).
Zips, Daniel et al., "New anticancer agents: in vitro and in vivo evaluation", In Vivo, 19:1-8 (2005).
Taber's Cyclopedic Medical Dictionary 1985 F. A. Davis Company Philadelphia p. 274.
Santa Cruz Biotechnology inc: "BECN1 (H-300): sc-11427" May 19, 2006 Retrieved from the internet: URL:http://datasheets.scbt.com/sc-11427.pdf retrieved on Mar. 10, 2010.
Santa Cruz Biotechnology inc: "BECN1 (E-8):sc-48341" Retrieved from the internet: URL:http://datasheets.scbt.com/sc-48341.pdf retrieved on Mar. 10, 2010.
ISR of PCT/IL2009/001150 mailed Mar. 30, 2010.
U.S. Appl. No. 13/132,589 Requirement for Restriction/Election Jul. 24, 2012.
U.S. Appl. No. 13/152,270 Requirement for Restriction/Election Feb. 14, 2012.
U.S. Appl. No. 13152,270 Non-Final Rejection Jun. 4, 2012.

* cited by examiner

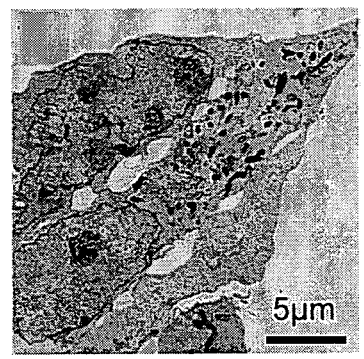
FIG. 5H
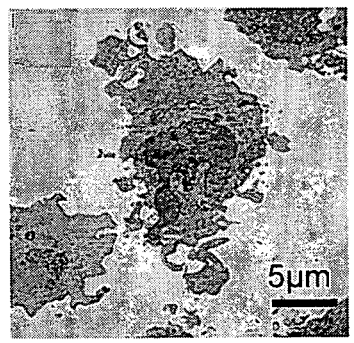 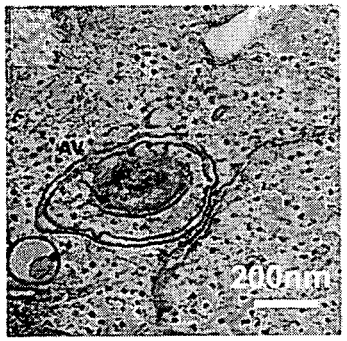 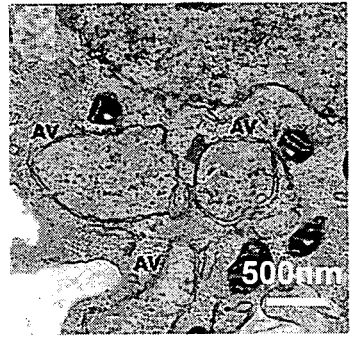
FIG. 5I  FIG. 5J  FIG. 5K

COMPOSITIONS AND METHODS FOR DIAGNOSING AND TREATING CANCER AND NEURODEGENERATIVE DISEASES RELATED TO BECLIN-1

RELATED APPLICATION DATA

This application is the continuation of PCT/IL2009/001150, filed Dec. 6, 2009, which claims the benefit of U.S. Provisional Patent Application Nos. 61/175,803, filed May 6, 2009 and 61/119,745, filed Dec. 4, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 16,511 byte ASCII (text) file named "Seq_List" created on Jun. 2, 2011.

FIELD OF THE INVENTION

The present invention relates to antibodies specific for human Beclin-1 protein phosphorylated at position Thr 119 useful in diagnosing diseases associated with impaired autophagy including cancer and neurodegenerative diseases. The invention further relates to human Beclin-1 mutated at position 119 with a phospho-mimicking residue and uses thereof in treating cancer and neurodegenerative diseases.

BACKGROUND OF THE INVENTION

Autophagy is a catabolic process conserved among all eukaryotes ranging from yeast to mammals. Autophagy is characterized by the formation of double membrane enclosed autophagosomes which engulf intracellular organelles and cytoplasmic constituents, and deliver them to the lysosomes for degradation. In addition to its cytoprotective functions in stressed cells (Levine and Kroemer, 2008, *Cell*, 132, 27-42), autophagy can serve as a cell death mechanism under some conditions (Berry and Baehrecke, 2007, *Cell*, 131, 1137-48; Gozuacik and Kimchi, 2007, *Curr. Top. Dev. Biol.*, 78, 217-45). Recent studies have demonstrated that autophagy is closely related to the occurrence and development of numerous pathological processes, including myopathy, neurodegenerative disorders, tuberculosis, cancer, type II diabetes and others. Beclin-1 was the first identified mammalian gene with a role in mediating autophagy. More and more evidence indicates that Beclin-1 loss or inactivation has a causative role for autophagy deficiencies in cancer formation (Bialik, S, and Kimchi, A. 2008, *Adv. Exp. Med. Biol.* 615:177-200). Conversely, Beclin-1 activation associated with autophagic induction is critical in pathologies associated with neurodegeneration either as a protective mechanism in mild activations or as an accelerator of cell death in prolonged/excessive/imbalanced activation of autophagy (Cherra and Chu, 2008, *Future Neurol.* 3:309-323. Balduini et al., 2009, *Autophagy* 5:221-3).

Beclin-1, a haplo-insufficient tumor suppressor which was initially identified as a Bcl-2 binding protein, is part of a class III PI3K multiprotein complex which participates in autophagosome nucleation. Beclin-1 interacts with several activators (Ambra-1, UVRAG, Bif-1), which positively regulate autophagy by promoting the activation of the PI3K protein, Vps34, and the formation of autophagosomes. The autophagy promoting activity of Beclin-1 is suppressed by anti-apoptotic members of the Bcl-2 family through direct binding. It has been recently reported that Beclin-1 is a bona fide BH3-only protein, and that the α-helix of its BH3 domain binds to the hydrophobic groove in Bcl-$X_L$ similar to the interactions previously shown for the other BH3 only proteins. Under normal steady state growth conditions Beclin-1 is bound to different Bcl-2 family members, whereas its dissociation from Bcl-2 is mediating autophagy (Pattingre et al., 2005, *Cell*, 122, 927-39).

The Role of Beclin-1 in Cancer

Many studies have suggested that changes in the autophagic activity and autophagic cell death are related to the occurrence and development of malignancy. These studies further indicated that the autophagy gene Beclin-1 plays an important role in the development of cancer through regulating the autophagic capacity of living cells. It was shown that Beclin-1 is commonly deleted in approximately 40% of prostate, 50% of breast, and 75% of ovarian cancers (Liang et al., 1999, *Nature*, 402, 672-676); moreover, decreased expression of Beclin-1 is also observed in other types of cancers including human colon cancer (Koneri™, et al., 2007, *Anticancer Research.*, 27, 1453-57) brain tumors (Miracco and Cosci, 2007, *Int J. Oncol.*, 30, 429-36) and hepatocellular carcinoma (Daniel et al., 2007, *Cancer Invest.*, 25, 226-31). This evidence indicated that the deletion of the Beclin-1 gene plays a causal role in promoting oncogenesis. It was further found that the protein level of Beclin-1 is lower in cervical cancer tissue than in normal tissue and is closely related to pelvic lymph node metastases and histological tumor grade (Wang et al., 2006, *J Sichuan Univ Med Sci Edi.*, 37, 860-863). In addition, Beclin-1 expression was found to be down-regulated in epithelial ovarian cancer tissues, and its overexpression can inhibit proliferation and induce apoptosis of cancer cell line SKOV3 in vitro (Duan et al., 2007, *Ai Zheng.*, 26, 258-63).

Beclin-1 levels appear to be one of the critical factors that affect the induction of autophagy, and as such has been suggested as a potential therapeutic target for cancer therapy. U.S. Pat. No. 6,432,914 discloses a method for treating ovarian cancer, breast cancer or prostate cancer by administering to the subject in need a therapeutically effective amount of Beclin-1 so as to restore cell growth control. U.S. Patent Application Publication No. 2005/276809 discloses a method for inducing autophagic cell death in a cancer cell, by administering a caspase 8 inhibitor and increasing the expression of Beclin-1. International Patent Application Publication No. WO 2006/082303 discloses a method to induce programmed cell death in a cancer patient by the administration of a motif of the Beclin-1 protein which can interact with an anti-apoptotic member of the family of Bcl-2 proteins.

The use of Beclin-1 was further suggested as a diagnostic tool for cancer. U.S. Pat. No. 5,858,669 discloses a method for identifying predisposition for cancer by identification of mutant Beclin-1 having reduced or lacking cellular proliferation inhibition activity. CN patent No. 1635144 discloses a method for diagnosing cancer susceptibility, specifically liver cancer, by detecting the expression levels of cancer related proteins selected from Beclin-1, L is 1, Pri51, RbAp48 or a combination thereof in an individual and comparing them with the normal expression levels of these proteins, wherein upregulated expression is indicative of cancer.

Beclin-1 and Neurodegenerative Diseases:

Intracellular accumulation of altered and misfolded proteins is the basis of most neurodegenerative disorders. Altered proteins are usually organized in the form of toxic multimeric complexes that eventually promote neuronal death. Cells rely on surveillance mechanisms that take care of the removal of these toxic products. Recent studies have shown that a primary failure in autophagy could be responsible for the accumulation of these altered proteins inside the affected neurons (Martinez-Vicente and Cuervo, 2007, *Lancet Neurol.* 6(4), 352-61). Other studies have found a correlation between the function of Beclin-1 and different neurodegenerative diseases. It was shown, for example, that the accumulation of mutant Huntingtin, critical for the pathogenesis of Huntington disease, is highly sensitive to the expression of Beclin-1. Moreover, the accumulated mutant Huntingtin recruits Beclin-1 and impairs the Beclin-1-mediated long lived protein turnover. It was further shown that the expression of Beclin-1 is decreased in an age-dependent fashion in human brains, proposing that the decrease of Beclin-1 expression may lead to a reduction of autophagic activity during aging, which in turn promotes the accumulation of mutant Huntingtin and the progression of the disease (Shibata et al., 2006, *J. Biol. Chem.,* 281, 14474-14485). In another example it was found that Beclin-1 is reduced by 60-70 percent in certain brain areas of Alzheimer's patients. It was shown that when Beclin-1 is reduced in early Alzheimer's disease, neurons produce more Amyloid precursor protein (APP), therefore regulating the Amyloid-beta accumulation, setting the stage for Alzheimer's pathology (Pickford et al., 2008, *Journal of Clinical Investigation,* 118(6), 2190-9).

Biomarkers for Neurodegenerative Diseases:

Neurodegenerative diseases like Alzheimer's and Parkinson's in their early stages are difficult for physicians to spot and many diagnoses are incorrect. Early and accurate diagnosis of neurodegenerative diseases is very important since early intervention may delay or arrest the reversible neuronal damage. Different examples for the diagnosis of neurodegenerative diseases, specifically Alzheimer's, using different biomarkers were described in the following patents: U.S. Pat. No. 6,703,212; EP Patent No. 1233979; U.S. Pat. No. 6,962, 793 and U.S. Pat. No. 7,348,149. Currently however, the only effective diagnostic method for these diseases consists of evaluating the cognitive function of the patient. The development of biochemical diagnostic markers that could aid in the diagnosis of neurodegenerative diseases in their early stages as well as for monitoring treatment is therefore highly desirable.

Thus, there is an unmet need for biomarkers of neurodegenerative diseases. With the identification of new, relevant bio-markers, such diseases could be treated prior to onset and in many cases prevent progression of symptoms, thus resulting in a significant extension of normal functional lifespan. As yet, however, the science of bio-markers is in its infancy and consequently diagnosis of neurodegenerative disease tends to occur after the patient has already suffered the majority of the neural damages.

Furthermore, although progress has been made in the identification of various potential cancer marker genes, as well as other biomolecular markers of cancer (e.g., Prostate-Specific Antigen in the case of Prostate cancer) there remains a continuing need for new marker genes along with their expressed proteins that can be used to specifically and selectively identify the appearance and pathogenic development of cancer in a patient. Providing additional means for early diagnosis of these diseases, as well as new therapeutic agents would thus be advantageous.

SUMMARY OF THE INVENTION

The present invention relates to antibodies specific for human Beclin-1 protein phosphorylated at Thr 119. The present invention further provides polynucleotides encoding same, expression vectors comprising them, and methods of diagnosing diseases or disorders associated with impaired autophagy including cancer and neurodegenerative diseases. The present invention further provides human Beclin-1 mutated at position 119 with a phospho-mimicking residue, polynucleotides encoding same and uses thereof in treating cancer and neurodegenerative diseases.

The present invention is based in part on the surprising discovery that Death Association Protein Kinase (DAPk) phosphorylates human Beclin-1 on the threonine residue 119, thus promoting the dissociation of Beclin-1 from its Bcl-2 inhibitors and inducing autophagy. Unexpectedly, substitution of the threonine residue at position 119 by glutamic acid resulted in the production of a human Beclin-1 variant, denoted T119E, having the ability to induce autophagy when overexpressed.

The phosphorylation of human Beclin-1 at position 119 is, therefore, crucial for promoting autophagy. A significant decrease in the concentration of phosphorylated human Beclin-1 in a cell is an indication for impaired autophagy which in turn is associated with cancer and neurodegenerative diseases. The invention surprisingly discloses that Thr119 phosphorylated human Beclin-1 and not human Beclin-1 itself is the crucial component for promoting autophagy and restoring cell growth control; therefore the ability to specifically detect the Thr119 phosphorylated protein provides new means for the diagnosis of cancer and neurodegenerative diseases. An antibody designed according to the principles of the present invention, to recognize the newly discovered epitope on phosphorylated Beclin-1, as detailed herein, is thus provided.

According to a first aspect, the present invention provides an antibody which has specific binding affinity for a phosphorylated human Beclin-1 protein, wherein the Thr residue at position 119 of the Beclin-1 protein is phosphorylated. According to one embodiment human Beclin-1 comprises the amino acid sequence as set forth in SEQ ID NO:1. According to some embodiments the antibody is polyclonal. According to other embodiments the antibody is monoclonal. The present invention further relates to fragments of the antibody of the invention which has specific binding affinity for a phosphorylated human-Beclin-1, wherein residue Thr 119 of the human Beclin-1 is phosphorylated According to another aspect, the present invention provides a method for diagnosing cancer and neurodegenerative diseases, comprising detecting the presence of Beclin-1 phosphorylated at position Thr 119 in a biological test sample. According to one embodiment, a reduced amount or absence of Beclin-1 phosphorylated at position Thr 119 in said biological test sample relative to the amount of Beclin-1 in a standard or control sample is indicative of cancer in said biological test sample. According to some embodiments, a reduced amount or absence of Beclin-1 phosphorylated at position Thr 119 in said biological test sample relative to the standard or control sample is indicative of a degenerative disease in said test sample. According to yet another embodiment, a reduced amount or absence of Beclin-1 phosphorylated at position Thr 119 in said biological test sample relative to the standard or control sample is indicative of an early stage of a degenerative disease in said test sample. According to another embodiment, the present invention provides a method for diagnosing cancer, comprising detecting the presence of Beclin-1 phosphorylated at position Thr 119 in a biological test sample using the antibody of the invention or antigen binding fragments thereof.

According to another embodiment, the present invention provides a method for diagnosing cancer, the method comprising:

a. obtaining a biological test sample;
b. contacting the test sample with an antibody of the invention, under conditions such that a complex can form between phosphorylated Beclin-1 and the antibody or antigen binding fragment thereof and quantifying the amount of the complex, thereby quantifying the amount of phosphorylated Beclin-1 in the biological test sample; and
c. comparing the amount of phosphorylated Beclin-1 in the biological test sample to a standard or control sample;
wherein a reduced amount or absence of phosphorylated Beclin-1 in said biological test sample relative to the standard or control sample is indicative of cancer in said test sample.

According to some embodiments the biological test sample is a tissue sample. According to other embodiments the tissue sample is derived from the breast, pancreas, stomach, liver, secretory gland, bladder, lung, skin, prostate gland, ovary, cervix, uterus, brain, eye, connective tissue, bone, muscles or vasculature. According to other embodiments the biological test sample is a tumor sample, or an isolate thereof. For example the tumor may be a breast tumor, a lung carcinoma, a colon carcinoma, a cervical carcinoma, an adenocarcinoma, a melanoma, a leukemia, a lymphoma, a glioma, a neuroblastoma, a retinoblastoma, and a sarcoma. According to other embodiments the biological test sample is a biological fluid or an isolate thereof. For example the biological fluid may be blood, serum or lymph.

According to certain embodiments, the tumor sample or biological fluid may comprise a tumor cell having reduced amounts of phosphorylated Beclin-1 protein relative to the amounts of phosphorylated Beclin-1 in cells of healthy subjects or normal cells surrounding the tumor. According to other embodiments, the tumor sample or biological fluid may comprise a tumor cell lacking phosphorylated Beclin-1. According to another embodiment, the method for diagnosing cancer of the present invention further comprises sequencing the gene encoding Beclin-1; or a transcript thereof in a biological sample, wherein a mutation at position Thr119 is indicative of cancer.

The present invention further provides a method for detecting a predisposition to cancer in a subject, comprising obtaining a DNA sample from the subject, and determining whether an alteration is present in the sequence encoding Beclin-1, wherein a mutation at position Thr 119 is indicative of a predisposition to cancer. According to another embodiment, the present invention provides a method for diagnosing a neurodegenerative disease, comprising detecting the presence of phosphorylated Beclin-1 in a biological test sample using the antibody of the invention.

According to another aspect, the present invention provides a method for diagnosing neurodegenerative disease, the method comprising:

a. obtaining a biological test sample;
b. contacting the test sample with an antibody of the invention under conditions such that a complex can form between phosphorylated Beclin-1 and the antibody and quantifying the amount of the complex, thereby quantifying the amount of phosphorylated Beclin-1 in the biological test sample; and
c. comparing the amount of phosphorylated Beclin-1 in the test sample to a standard or control sample;
wherein a reduced amount or absence of phosphorylated Beclin-1 in the biological test sample relative to the standard or control sample is indicative of the neurodegenerative disease in said test sample.

According to another embodiment the neurodegenerative disease diagnosed by the method of the present invention includes for example Alzheimer's disease, Huntington's disease, Parkinson's disease, neurodegeneration due to stroke, amyotrophic lateral sclerosis, Pick's disease, Progressive Supranuclear Palsy (PSP), fronto-temporal dementia (FTD), pallido-ponto-nigral degeneration (PPND), Guam-ALS syndrome, pallido-nigro-luysian degeneration (PNLD) and cortico-basal degeneration (CBD).

According to another embodiment the biological test sample comprises at least one cell type selected from the group consisting of circulating lymphocytes and cells isolated from cerebro spinal fluid. According to other embodiments the biological test sample comprises a cell selected from the group consisting of olfactory neuroepithelial neuronal cell bodies or their neuronal processes (i.e., dendrites and axon of a neuron) and hippocampal cells said cells expressing Beclin-1 protein in healthy subjects.

According to some embodiments of the present invention, the amount of phosphorylated Beclin-1 is determined by a method selected from the group consisting of immunohistochemistry, immunostaining and immunofluorescence assays. According to other embodiments the amount of phosphorylated Beclin-1 in cell extracts is determined by a western blot analysis. According to some embodiments of the present invention the test sample is from a human subject.

According to another embodiment, the method for diagnosing a degenerative disease according to certain embodiments of the present invention, further comprises sequencing the gene encoding Beclin-1; or a transcript thereof in a biological test sample, wherein a mutation at position Thr119 is indicative of a degenerative disease.

The present invention further provides a method for detecting a predisposition to a degenerative disease in a subject, comprising obtaining a DNA sample from the subject, and determining whether an alteration is present in the sequence encoding Beclin-1, wherein a mutation at position Thr 119 is indicative of a predisposition to a neurodegenerative disease.

According to another aspect, the present invention provides a human Beclin-1 variant, wherein threonine at position 119 of said human Beclin-1 variant is substituted with a phospho-mimicking residue. According to one embodiment, the phospho-mimicking residue is a glutamic acid residue (e.g. SEQ ID NO:2). According to another embodiment, the phospho-mimicking residue is an aspartic acid (e.g. SEQ ID NO:3).

A "phospho-mimicking residue" as used herein refers to a residue which is not phosphorylated but displays physico-chemico properties similar to a residue carrying a phosphate ion (phosphorylated residue). According to one embodiment, the phospho-mimicking residue is negatively charged. According to another embodiment the phospho-mimicking residue is negatively charged at pH above the pI of the phospho-mimicking residue. According to another embodiment, the phospho-mimicking residue is negatively charged at physiological pH (pH=7.4).

According to another embodiment the present invention provides an isolated polynucleotide encoding a human Beclin-1 variant, wherein threonine at position 119 of the human Beclin-1 variant is substituted with a phospho-mimicking residue. According to another embodiment, the present invention provides an isolated polynucleotide encoding a human Beclin-1 variant, wherein threonine at position 119 of said human Beclin-1 variant is substituted with a glutamic acid residue. According to another embodiment, the present invention provides an isolated polynucleotide encoding a human Beclin-1 variant, wherein threonine at position 119 of said human Beclin-1 variant is substituted with an aspartic acid residue. According to some embodiments, the human Beclin-1 variants of the present invention are capable of inducing autophagy. According to some other embodiments, the human Beclin-1 variants are capable of inducing autophagic cell death. According to yet some other embodiments, the human Beclin-1 variants are capable of restoring cell growth control.

According to another aspect, the present invention provides a human Beclin-1 variant, wherein threonine at position 119 of said Beclin-1 variant is substituted with a phosphosilencing residue. According to one embodiment the phosphor-silencing residue is an alanine (e.g. SEQ ID NO:4). A "phospho-silencing residue" as used herein refers to a residue which is incapable of phosphorylation.

According to another embodiment, the present invention provides a recombinant polynucleotide construct wherein a polynucleotide encoding a human Beclin-1 variant of the present invention, is operably linked to a transcription regulating sequences that will direct the transcription of the polynucleotide in the intended host cell. In another embodiment, the transcription regulating sequences are transcription initiation regulating sequences. The invention further provides a vector comprising a recombinant polynucleotide construct encoding a human Beclin-1 variant of the invention. According to various embodiments the vector is for example, a plasmid or a virus. The recombinant polynucleotide construct may be expressed in a host cell selected from eukaryotic and prokaryotic.

According to another embodiment, the present invention provides a pharmaceutical composition comprising as an active ingredient a recombinant polynucleotide construct comprising an isolated polynucleotide encoding a human Beclin-1 variant having a phospho-mimicking residue at position 119.

According to another embodiment, the present invention provides a method for treating cancer or inhibiting tumor progression in a subject in need thereof comprising expressing in cells of the subject a human Beclin-1 variant having a phospho-mimicking residue at position 119. According to some embodiments the expression of the human Beclin-1 variant having a phospho-mimicking residue at position 119 in cells of the subject induces autophagy, thereby treating cancer or inhibiting tumor progression in the subject. According to some other embodiments, the expression of the human Beclin-1 variant having a phospho-mimicking residue at position 119 in cells of the subject induces cell death, thereby treating cancer or inhibiting tumor progression in the subject. According to some other embodiments, the expression of the human Beclin-1 variant having a phospho-mimicking residue at position 119 in cells of the subject restores cell growth control, thereby treating cancer or inhibiting tumor progression in the subject.

According to another embodiment, the method for treating cancer or inhibiting tumor progression comprises the administration to a subject of a therapeutically effective amount of a recombinant polynucleotide construct comprising a polynucleotide encoding the human Beclin-1 variant having a phospho-mimicking residue at position 119. According to another embodiment, the recombinant polynucleotide construct is introduced into the subject's cells ex vivo. According to another embodiment, the recombinant polynucleotide construct is introduced into the subject's cells in vivo.

According to another embodiment, the subject to be treated by methods and compositions of the present invention has a tumor characterized by at least one of the following: (1) reduced expression or activity of death associated protein kinase (DAPk) in at least a portion of the cells of the tumor as compared to the expression or activity of DAPk in healthy cells or tissues; (2) reduced amount of wild type Beclin-1 (as set forth in SEQ ID NO:1) in at least a portion of the cells of the tumor as compared to the amount of wt in healthy cells or tissues.

According to another embodiment, the subject to be treated by methods and composition of the present invention is selected from the group consisting of a subject displaying pathology resulting from cancer, a subject suspected of displaying pathology resulting from cancer, and a subject at risk of displaying pathology resulting from cancer.

According to another embodiment, the present invention provides a method of selectively inducing, enhancing or promoting autophagy in target cells, comprising expressing in target cells a polynucleotide encoding a human Beclin-1 variant of the invention.

According to some embodiments the target cells are cells in which the expression or activity of DAPk is absent or significantly reduced. According to some other embodiments the target cells comprise human Beclin-1 unable to induce autophagy. According to yet some other embodiments the target cell is a cancer cell.

The present invention further provides the use of the recombinant polynucleotide construct according to some embodiments of the invention for the manufacture of a medicament for treating cancer or inhibiting tumor progression in a subject. According to some embodiments the subject has a tumor characterized by significantly reduced expression of wild type Beclin-1 as set forth in SEQ ID NO:1 in at least a portion of the cells of the tumor relative to the expression of said wild type Beclin-1 in a cell of a healthy subject.

The present invention further provides a method of screening for a molecule that influences the intracellular concentration of human Beclin-1 phosphorylated at residue threonine 119, comprising:
 a. adding a putative molecule to a cell expressing human Beclin-1;
 b. contacting the cell with an antibody of the invention or antigen binding fragment thereof, under conditions such that a complex can form between phosphorylated Beclin-1 and the antibody and quantifying the amount of the complex, thereby quantifying the amount of phosphorylated Beclin-1 in the biological test sample; and
 c. comparing the amount of phosphorylated Beclin-1 in the cell in the presence and absence of said putative molecule.

According to one embodiment, the putative molecule increases the intracellular concentration of the Thr119 phosphorylated human Beclin-1. According to another embodiment, the putative molecule decreases the intracellular concentration of the Thr119 phosphorylated human Beclin-1.

The present invention further provides a molecule obtained by the screening methods of the invention, wherein said molecule increases the intracellular concentration of Beclin-1 phosphorylated at position Thr119, for use in the treatment of cancer. The present invention further provides a molecule obtained by the screening methods of the invention, wherein said molecule increases the intracellular concentration of Beclin-1 phosphorylated at position Thr119, for use in the treatment of a neurodegenerative disease.

According to another aspect, the present invention provides a kit for analyzing the level of Beclin-1 that is phosphorylated at position Thr 119 in a biological test sample; the kit comprises the antibody of the invention. In one embodiment, the kit is identified for diagnosing cancer. In another embodiment the kit is identified for diagnosing degenerative diseases. In some embodiments, the kit contains, in addition to the antibody according to the invention, additional reagents such as buffers, solutions for sample preparation, solutions for detecting the reagent, including instructions for use for carrying out the test.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description

DETAILED DESCRIPTION OF THE INVENTION

Figure 1A:
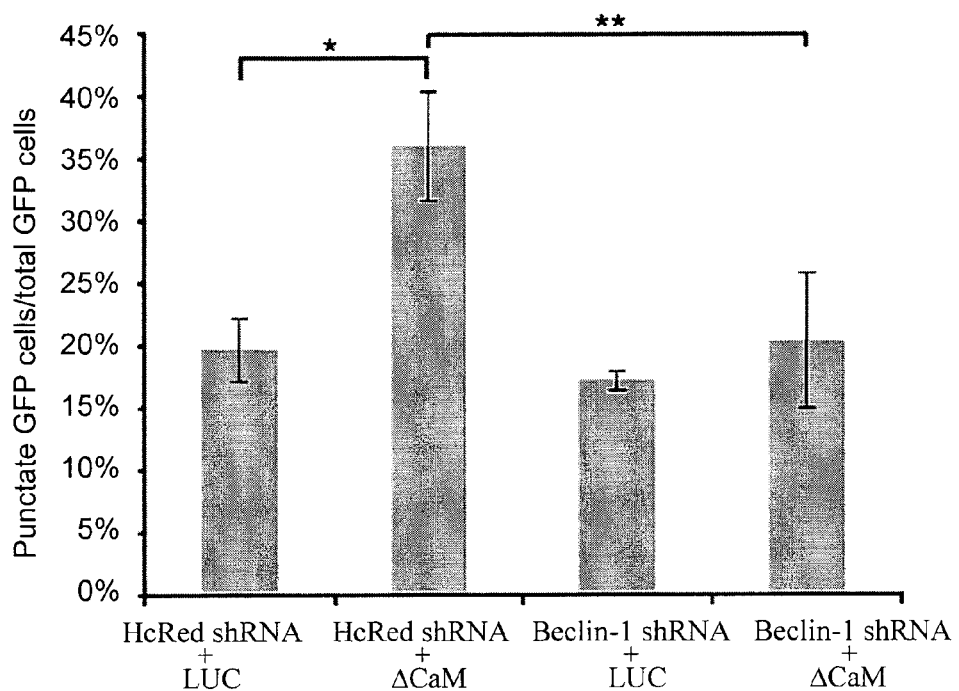
FIG. 1A-D: Beclin-1 is required for DAPk-induced autophagy: The frequency of cells in which GFP-LC3 appeared in puncta increased over basal levels when ΔCaM DAPk was introduced to the cells (A, B and C) and was significantly reduced by knocking down Beclin-1. Data presented are the mean±SD from triplicates of 100 transfected cells. Single and double asterisks denote significance level of p=0.001 (A). Western blot analysis was performed using the indicated antibodies (B). Representative GFP-LC3 staining of cells transfected with the control shRNA-HcRed together with pcDNA3-luciferase (C) or ΔCaM DAPk (D).
Figure 1B:
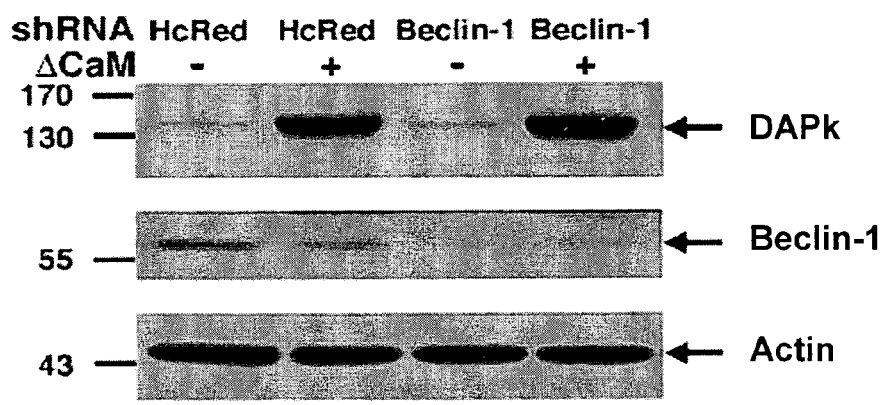
Figure 1C:
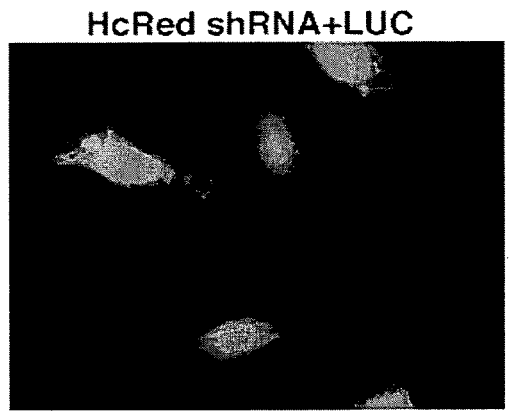
Figure 1D:
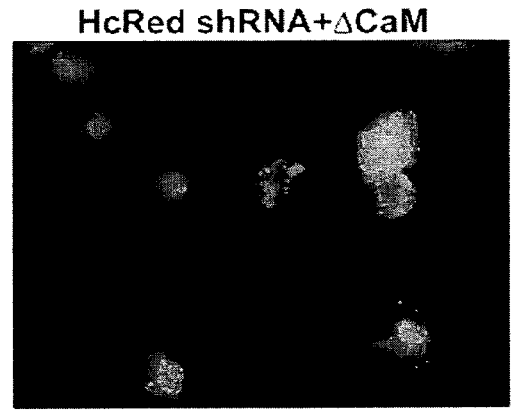

The present invention relates to antibodies specific for human Beclin-1 protein phosphorylated at position Thr 119 (also denoted herein as Thr119 or T119). The present invention is based in part on the finding that Beclin-1 is a substrate for the death associated protein kinase (DAPk), and that DAPk is phosphorylating Beclin-1 at residue Thr119 located at Beclin's BH3 domain. DAPk was found to significantly reduce the amounts of Bcl-XL which were immunoprecipitated by wild type Beclin-1, whereas it failed to reduce Bcl-XL binding to the T119A phospho-silencing mutant, thus conferring a functional role to the phosphorylation event. It was further found that a T119E phospho-mimicking mutant displayed a weaker association with Bcl-XL and Bcl-2 compared to wild type Beclin-1, and could induce autophagy when overexpressed. Altogether these data suggested that the phosphorylation of Beclin-1 on position Thr119 leads to Beclin's dissociation from its Bcl-2 family inhibitors such as Bcl-XL and Bcl-2, resulting in autophagy induction.

Thr119 is a unique residue to Beclin-1's BH3 domain, since in other BH3-only proteins a hydrophobic residue exists in this site. Without wishing to be bound by any theory or mechanism of action, this hydrophobic residue acts together with three additional hydrophobic residues present in their BH3 amphipathic α-helix to stabilize the interaction with the hydrophobic residues in the target-binding pocket. "Autophagy" as used herein refers to a variety of tightly-regulated catabolic processes which involve the degradation of a cell's own components through the lysosomal machinery and play a normal part in cell growth, development, and homeostasis, helping to maintain a balance between the synthesis, degradation, and subsequent recycling of cellular products. The most well-known catabolic process of autophagy involves the formation of a membrane around a targeted region of the cell, separating the contents from the rest of the cytoplasm. The resultant vesicle then fuses with a lysosome and subsequently degrades the contents.

Antibodies

According to a first aspect, the present invention provides an antibody specific for a phosphorylated human Beclin-1, wherein the phosphorylation is at Thr 119. According to one embodiment human Beclin-1 comprises the amino acid sequence as set forth in SEQ ID NO:1. According to another embodiment the antibody is polyclonal. According to another embodiment the antibody is monoclonal.

The term "antibody" is used in the broadest sense and specifically covers antibodies (including full length monoclonal antibodies) and antibody fragments so long as they recognize human Beclin-1 which is phosphorylated at position Thr119. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab')2, and Fv fragments; diabodies; linear antibodies; single-chain antibody molecules; and multispecific antibodies formed from antibody fragments.

As used herein, the term "antigen" is used in reference to any substance that is capable of being recognized by an antibody. It is intended that this term encompass any antigen and "immunogen" (i.e., a substance which induces the formation of antibodies). Thus, in an immunogenic reaction, antibodies are produced in response to the presence of an antigen or portion of an antigen. The terms "antigen" and "immunogen" are used to refer to an individual macromolecule or to a homogeneous or heterogeneous population of antigenic macromolecules. It is intended that the terms antigen and immunogen encompass protein molecules or portions of protein molecules, which contains one or more epitopes. The term "epitope" as used herein, refers to that fragment of a molecule that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as "epitopes" or "antigenic determinants". An antigenic determinant may compete with the intact antigen (i.e., the immunogen used to elicit the immune response) for binding to an antibody.

The term "monoclonal antibody" (MAb) as used herein refers to antibodies that are highly specific, being directed against a single antigenic site. It further refers to an antibody obtained from a population of substantially homogeneous antibodies, i.e., the individual antibodies comprising the population are identical except for possible naturally-occurring mutations that may be present in minor amounts.

The term "polyclonal antibody" as used herein denotes a mixture of different antibody molecules which react with more than one immunogenic determinant of an antigen.

MAbs may be obtained by methods known to those skilled in the art. See, for example Kohler et al (1975); U.S. Pat. No. 4,376,110; Ausubel et al (1987-1999); Harlow et al (1988); and Colligan et al (1993), the contents of which references are incorporated entirely herein by reference. The mAbs of the present invention may be of any immunoglobulin class including IgG, IgM, IgE, IgA, and any subclass thereof. A hybridoma producing an mAb may be cultivated in vitro or in vivo. High titers of mAbs can be obtained in in vivo production where cells from the individual hybridomas are injected intraperitoneally into pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

Besides the conventional method of raising antibodies in vivo, antibodies can be generated in vitro using phage display technology. Such a production of recombinant antibodies is much faster compared to conventional antibody production and they can be generated against an enormous number of antigens. In contrast, in the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on phage display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library.

An aspect of some embodiments of the present invention provides a method for diagnosing cancer, comprising determining the level Beclin-1 that is phosphorylated at position Thr119 in a biological test sample using the antibody of the invention, the method comprising:

a. obtaining a biological test sample;
b. contacting the test sample with an antibody of the invention under conditions such that a complex can form between Beclin-1 phosphorylated at position Thr119 and the antibody or antigen binding fragment thereof and quantifying the amount of the complex, thereby quantifying the amount of phosphorylated Beclin-1 in the biological test sample; and
c. comparing the amount of phosphorylated Beclin-1 in the biological test sample or isolate of the test sample to a standard or control sample;

According to one embodiment a reduction in the amount of Beclin-1 phosphorylated at position Thr119 in a biological test sample relative to a standard or control sample, is indicative of cancer in said biological test sample. According to some embodiments the amount of Beclin-1 phosphorylated at position Thr 119 is reduced by at least 20% relative to a standard or control sample. According to some other embodiments the amount of Beclin-1 phosphorylated at position Thr 119 is reduced by at least 25% relative to a standard or control sample. According to some embodiments the amount of Beclin-1 phosphorylated at position Thr 119 is reduced by at least 30% relative to a standard or control sample. According to some embodiments the amount of Beclin-1 phosphorylated at position Thr 119 is reduced by at least 35% relative to a standard or control sample. According to some embodiments the amount of Beclin-1 phosphorylated at position Thr 119 is reduced by at least 40% relative to a standard or control sample. According to some embodiments the amount of Beclin-1 phosphorylated at position Thr 119 is reduced by at least 45% relative to a standard or control sample. According to some embodiments the amount of Beclin-1 phosphorylated at position Thr 119 is reduced by at least 50% relative to a standard or control sample. According to some embodiments the amount of Beclin-1 phosphorylated at position Thr 119 is reduced by at least 55% relative to a standard or control sample. According to some embodiments the amount of Beclin-1 phosphorylated at position Thr 119 is reduced by at least 60% relative to a standard or control sample. According to some embodiments the amount of Beclin-1 phosphorylated at position Thr 119 is reduced by at least 70% relative to a standard or control sample. According to some embodiments the amount of Beclin-1 phosphorylated at position Thr 119 is reduced by at least 80% relative to a standard or control sample. According to some embodiments the amount of Beclin-1 phosphorylated at position Thr 119 is reduced by at least 90% relative to a standard or control sample. According to another embodiment the absence of Beclin-1 phosphorylated at position Thr119 in a biological test sample is indicative of cancer in said biological test sample. According to some embodiments, the standard or control sample may be taken from a healthy subject or from a healthy tissue of a subject As used herein, a "biological test sample" refers to a sample of biological material obtained from a subject, preferably a human subject, or present within a subject, preferably a human subject, including a tissue, tissue sample, or cell sample (e.g., a tissue biopsy, for example, an aspiration biopsy, a brush biopsy, a surface biopsy, a needle biopsy, a punch biopsy, an excision biopsy, an open biopsy, an incision biopsy or an endoscopic biopsy), tumor, tumor sample, or biological fluid (e.g., blood, serum, lymph, cerebral spinal fluid). As used herein, a "tissue sample" refers to a portion, piece, part, segment, or fraction of a tissue which is obtained or removed from an intact tissue of a subject, preferably a human subject. For example, tissue samples can be obtained from the breast, pancreas, stomach, liver, secretory gland, bladder, lung, skin, prostate gland, breast ovary, cervix, uterus, brain, eye, connective tissue, bone, muscles or vasculature. In another embodiment, the biological test sample is a tumor sample (e.g., a tumor biopsy).

As used herein, a "tumor sample" refers to a portion, piece, part, segment, or fraction of a tumor, for example, a tumor which is obtained or removed from a subject (e.g., removed or extracted from a tissue of a subject), preferably a human subject. A tumor sample can be obtained from a solid tumor as well as from a non-solid tumor, for example, from a breast carcinoma, a lung carcinoma, squamous cell carcinoma, basal cell carcinoma, a colon carcinoma, a cervical carcinoma, Kaposi sarcoma, prostate carcinoma, an adeno carcinoma, a melanoma, hemangioma, meningioma, astrocytoma, neuroblastoma, carcinoma of the pancreas, gastric carcinoma, colorectal carcinoma, colon carcinoma, transitional cell carcinoma of the bladder, carcinoma of the larynx, chronic myeloid leukemia, acute lymphocytic leukemia, acute promyelocytic leukemia, multiple myeloma, T-cell lymphoma, B-cell lymphomas, retinoblastoma, sarcoma gallbladder, bronchial and skin cancers. In another embodiment, the tumor sample is obtained from a primary tumor (e.g., is a primary tumor sample). In another embodiment, the biological test sample is obtained from a metastatic lesion (e.g., is a metastatic lesion sample).

The term "tumor" as used herein denotes an uncontrolled growing mass of abnormal cells. This term includes both primary tumors, which may be benign or malignant, as well as secondary tumors, and metastases, which have spread to other sites in the body. The tumor may be a solid tumor or a non-solid tumor.

The present invention also encompasses the use of isolates of a biological test sample in the methods of the invention. As used herein, an "isolate" of a biological test sample (e.g., an isolate of a tissue or tumor sample) refers to a material or composition (e.g., a biological material or composition) which has been separated, derived, extracted, purified or isolated from the sample and preferably is substantially free of undesirable compositions and/or impurities or contaminants associated with the biological test sample. Preferred isolates include, but are not limited to, DNA (e.g., cDNA or genomic DNA). RNA (e.g., mRNA), and protein (i.e., purified protein, protein extracts, polypeptides).

According to another embodiment, the method for diagnosing cancer of the present invention, further comprises the sequencing the gene encoding Beclin-1 in a biological test sample or isolate of a sample, wherein the presence of a mutation at position Thr119 is indicative of cancer. According to another embodiment, mutation at position Thr119 is indicative of a degenerative disease. According to another embodiment a direct DNA sequencing method will be used using for example an automated DNA sequencer. According to some other embodiments the analysis of the gene encoding Beclin-1 include known in the art methods such as DNA arrays or microarrays, SAGE (serial analysis of gene expression), READS (restriction enzyme amplification of digested cDNAs), TOGA (total gene expression analysis), protein arrays and proteomics, expressed sequence tag (EST) sequencing, subtractive RNA fingerprinting (SuRF), subtractive cloning, differential display (DD), comparative genomic hybridization, FISH (fluorescent in situ hybridization) techniques and mass spectrometry methods.

Another aspect of some embodiments of the present invention provides a method for diagnosing neurodegenerative disease, comprising detecting the presence of phosphorylated Beclin-1 in a biological test sample using the antibody of the invention, the method comprising:
  a. obtaining a biological test sample;
  b. contacting the test sample with an antibody of the invention under conditions such that a complex can form between phosphorylated Beclin-1 and the antibody or antigen binding fragment thereof and quantifying the amount of the complex, thereby quantifying the amount of phosphorylated Beclin-1 in the biological sample; and
  c. comparing the amount of phosphorylated Beclin-1 in the sample to a standard or control sample;

According to one embodiment a reduction in the amount of Beclin-1 phosphorylated at position Thr119 in a biological test sample relative to a standard or control sample, is indicative of a degenerative disease in said biological test sample. According to another embodiment, a reduction in the amount of Beclin-1 phosphorylated at position Thr119 in a biological test sample relative to a standard or control sample, is indicative of an early stage of a degenerative disease in said test sample. According to some embodiments the amount of Beclin-1 phosphorylated at position Thr 119 is reduced by at least 20% relative to a standard or control sample. According to some other embodiments the amount of Beclin-1 phosphorylated at position Thr 119 is reduced by at least 25% relative to a standard or control sample. According to some embodiments the amount of Beclin-1 phosphorylated at position Thr 119 is reduced by at least 30% relative to a standard or control sample. According to some embodiments the amount of Beclin-1 phosphorylated at position Thr 119 is reduced by at least 35% relative to a standard or control sample. According to some embodiments the amount of Beclin-1 phosphorylated at position Thr 119 is reduced by at least 40% relative to a standard or control sample. According to some embodiments the amount of Beclin-1 phosphorylated at position Thr 119 is reduced by at least 45% relative to a standard or control sample. According to some embodiments the amount of Beclin-1 phosphorylated at position Thr 119 is reduced by at least 50% relative to a standard or control sample. According to some embodiments the amount of Beclin-1 phosphorylated at position Thr 119 is reduced by at least 55% relative to a standard or control sample. According to some embodiments the amount of Beclin-1 phosphorylated at position Thr 119 is reduced by at least 60% relative to a standard or control sample. According to some embodiments the amount of Beclin-1 phosphorylated at position Thr 119 is reduced by at least 70% relative to a standard or control sample. According to some embodiments the amount of Beclin-1 phosphorylated at position Thr 119 is reduced by at least 80% relative to a standard or control sample. According to some embodiments the amount of Beclin-1 phosphorylated at position Thr 119 is reduced by at least 90% relative to a standard or control sample. According to another embodiment the absence of Beclin-1 phosphorylated at position Thr119 in a biological test sample is indicative of a neurodegenerative disease.

"Neurodegenerative disease" as used herein, refers to a condition associated with central or peripheral nervous system characterized by progressive, gradual, loss of functional neural tissue.

As used herein 'early stage of a neurodegenerative disease' refers according to one embodiment to stage or stages of the neurodegenerative disease in which no cognitive decline or a very mild cognitive decline is observed during medical examination by a health care professional. According to other embodiments 'early stages of a neurodegenerative disease' refer to stages in which the amount of Beclin-1 phosphorylated at position Thr 119 in a biological test sample is lower relative to a standard or control sample taken from a healthy subject or from a healthy tissue of a subject.

According to another embodiment the neurodegenerative disease diagnosed by the method of the present invention is selected from but not limited the group consisting of Alexander disease, Ataxia telangiectasia, Alper's disease, Alzheimer's disease, Batten disease (also known as Spielmeyer-Vogt-Sjogren-Batten disease), Canavan disease, Cockayne syndrome, Corticobasal degeneration, Creutzfeldt-Jakob disease, Bovine spongiform encephalopathy (BSE), Huntington's disease, HIV-associated dementia, Kennedy's disease, Krabbe disease Lewy body dementia, Machado-Joseph disease (Spinocerebellar ataxia type 3), Multiple System Atrophy, Narcolepsy, Neuroborreliosis, Pelizaeus-Merzbacher Disease, Primary lateral sclerosis, Prion diseases, Parkinson's disease, neurodegeneration due to stroke, amyotrophic lateral sclerosis, Pick's disease, Progressive Supranuclear Palsy (PSP), fronto-temporal dementia (FTD), pallido-ponto-nigral degeneration (PPND), Guam-ALS syndrome, pallido-nigro-luysian degeneration (PNLD) Refsum's disease, Sandhoff disease, Schilder's disease and cortico-basal degeneration (CBD).

As used herein, the terms a "biological test sample", a "biological sample" or a "test sample" refer to a sample comprising a cell obtained from a subject, preferably a human subject, or present within a subject, the cell selected from the group consisting of circulating lymphocytes, cells isolated from cerebral spinal fluid, olfactory neuroepithelial neuronal cell bodies or their neuronal processes, and hippocampal cells, said cell expressing Beclin-1 protein in healthy subjects. According to several embodiments of methods of the present invention, the amount of phosphorylated Beclin-1 is determined by a method selected from the group consisting of radioimmunoassay, immunohistochemistry, immunostaining and immunofluorescence assay.

Immunohistochemistry as used herein refers to a method which involves detection of a substrate in situ in fixed cells by substrate specific antibodies according to embodiments of the present invention. The substrate specific antibodies may be linked to fluorophores (as in the case of immunofluorescence). Detection is by microscopy and subjective or automatic evaluation. It will be appreciated that immunohistochemistry is often followed by counterstaining of the cell nuclei using for example Hematoxylin or Giemsa stain.

Immunoassays may be carried out in liquid or on biological support. For instance, a sample (e.g., blood, plasma, stool, urine, cells, tissue, cerebral spinal fluid, body fluids, etc.) can be brought in contact with a solid phase support or carrier (such as nitrocellulose or plastic) that comprises an antibody of the invention capable of specifically recognizing human Beclin-1 phosphorylated at position Thr119. The support may then be contacted with a second antibody, which recognizes preferably a second site different from the site recognized and bound by the antibody of the invention or antigen binding fragments thereof. The second antibody can be detectably labeled, e.g., with a fluorescent label or an enzyme, or it can be labeled by a secondary labeling reagent that binds to it specifically, and then its presence measured by conventional means for detecting the label.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, and polyacrylamides. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc.

Beclin-1 Variants

According to a second aspect, the present invention provides a human Beclin-1 variant, wherein threonine at position 119 of said human Beclin-1 variant is substituted with a phospho-mimicking residue. According to one embodiment, the phospho-mimicking residue is a glutamic acid residue (e.g. SEQ ID NO:2). According to another embodiment, the phospho-mimicking residue is an aspartic acid residue (e.g. SEQ ID NO:3). According to another embodiment, the present invention provides an isolated polynucleotide encoding a human Beclin-1 variant, wherein threonine at position 119 of the human Beclin-1 variant is substituted with a phospho-mimicking residue. According to a preferred embodiment, the phospho-mimicking residue is selected from glutamic acid and aspartic acid. According to another embodiment, the human Beclin-1 variants of the present invention are capable of inducing autophagy. According to another embodiment, the human Beclin-1 variants are capable of inducing cell death. Without wishing to be bound my mechanism of action the human Beclin-1 variants are capable of inducing autophagic cell death. According to yet another preferred embodiment, the human Beclin-1 variants are capable of restoring cell growth control. According to a further embodiment, the human Beclin-1 variants are capable of treating a subject unable to control autophagy in the cells of the subject. In a specific embodiment, the cells are cancerous.

A "phospho-mimicking residue" as used herein refers to a residue which is not phosphorylated but displays physico-chemico properties similar to a residue carrying a phosphate ion (phosphorylated residue). According to one embodiment, the phospho-mimicking residue is negatively charged. According to another embodiment the phospho-mimicking residue is negatively charged at pH above the pI of the phospho-mimicking residue. According to another embodiment, the phospho-mimicking residue is negatively charged at physiological pH (pH=7.4).

In another embodiment, the phospho-mimicking residue is a glutamic acid. According to another embodiment the sequence of human Beclin-1 carrying a glutamic acid at position Thr119 comprises the amino acid sequence as set forth in SEQ ID NO:2. According to another embodiment human Beclin-1 variant is a homolog of SEQ ID NO: 2. In another embodiment, the human Beclin-1 variant sequence is a fragment of SEQ ID NO: 2. In another embodiment, the human Beclin-1 variant sequence is a homolog of a fragment of SEQ ID NO: 2. In different embodiments, "homolog" may refer e.g. to any degree of homology disclosed herein. Each possibility represents a separate embodiment of the present invention.

As used herein, the term "variant" refers to substantially similar sequences possessing common qualitative biological activities. An oligonucleotide variant includes a homolog, analog, extension or fragment of a nucleotide sequence useful for the invention. Encompassed within the term "variant" are chemically modified natural and synthetic nucleotide molecules (derivatives). Also encompassed within the term "variant" are substitutions (conservative or non-conservative), additions or deletions within the nucleotide sequence of the molecule, as long as the required function is sufficiently maintained. Polynucleotides variants may share at least 50%, 55%, 60%, 65%, 70%, 75%, 80%, 85%, 90%, 95%, 96%, 97%, 98% or 99% sequence identity (homology). In different embodiments, "homolog" may refer e.g. to any degree of homology disclosed herein.

Various methods of introducing isolated polynucleotide into cells exist and are well-known in the art. In one example, one can introduce the isolated polynucleotide by (a) recovering cancer cells from the subject, (b) introducing the isolated polynucleotide encoding a human Beclin-1 variant, wherein threonine at position 119 of the human Beclin-1 variant is substituted with a phospho-mimicking residue into the cells; and (c) reintroducing the cells of step (b) into the subject so as to treat the subject who has cancer.

The term "polynucleotide" as used herein refers to an oligonucleotide, polynucleotide or nucleotide and fragments or portions thereof, and to DNA or RNA of genomic or synthetic origin, which may be single- or double-stranded, and represent the sense or antisense strand. The term should also be understood to include, as equivalents, analogs of either RNA or DNA made from nucleotide analogs, and, as applicable to the embodiment being described.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a peptide or protein if transcription and translation of mRNA corresponding to that gene produces the peptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the peptide or protein or other product of that gene or cDNA The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into elongating polypeptides of the invention. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

A polynucleotide of the present invention can be produced using recombinant DNA technology (e.g., polymerase chain reaction (PCR) amplification, cloning) or chemical synthesis. Nucleic acid sequences include natural nucleic acid sequences and homologs thereof, comprising, but not limited to, natural allelic variants and modified nucleic acid sequences in which nucleotides have been inserted, deleted, substituted, and/or inverted in such a manner that such modifications do not substantially interfere with the nucleic acid molecule's ability to encode the recombinant polypeptides of the present invention.

As used herein, the term "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

As used herein, the term "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. Selectable markers include, for example, sequences conferring antibiotic resistance markers, which may be used to obtain successful transformants by selection, such as ampicillin, tetracycline and kanamycin resistance sequences, or supply critical nutrients not available from complex media. The expression vector further comprises a promoter. In the context of the present invention, the promoter must be able to drive the expression of the polypeptide within the cells. Many viral promoters are appropriate for use in such an expression vector (e.g., retroviral ITRs, LTRs, immediate early viral promoters (IEp) (such as herpes virus IEp (e.g., ICP4-IEp and ICP0-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters. Suitable expression vectors may be plasmids derived, for example, from pBR322 or various pUC plasmids, which are commercially available. Other expression vectors may be derived from bacteriophage, phagemid, or cosmid expression vectors, all of which are described in sections 1.12-1.20 of Sambrook et al., (Molecular Cloning: A Laboratory Manual. $3^{rd}$ edn., 2001, Cold Spring Harbor Laboratory Press). Isolated plasmids and DNA fragments are cleaved, tailored, and ligated together in a specific order to generate the desired vectors, as is well known in the art (see, for example, Sambrook et al., ibid).

Methods for manipulating a vector comprising an isolated polynucleotide are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the polynucleotide of interest is introduced into the cells by any means appropriate for the transfer of DNA into cells. Many such methods are well known in the art (e.g., Sambrook et al., supra; see also Watson et al., 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion. Examples of eukaryotic cells into which the expression vector can be introduced include, but are not limited to, ovum, stem cells, blastocytes, and the like.

According to another embodiment, the present invention provides a recombinant polynucleotide construct wherein a polynucleotide encoding any of the human Beclin-1 variants of the present invention, is operably linked to a transcription regulating sequences that will direct the transcription of the polynucleotide in the intended host cell. In another embodiment, the transcriptional regulating sequences are transcriptional initiation regulating sequences. The invention further provides vectors comprising the recombinant polynucleotide constructs encoding the human Beclin-1 variants of the invention, the vector being a plasmid or a virus. Consequently, the recombinant polynucleotide construct may be expressed in a host cell selected from eukaryotic and prokaryotic.

Pharmaceutical Compositions

According to some embodiments, the present invention provides a pharmaceutical composition comprising as an active ingredient the recombinant polynucleotide construct comprising the isolated polynucleotide encoding the human Beclin-1 variants according to embodiments of the invention and a pharmaceutically acceptable carrier, excipient or diluent.

As used herein, a "pharmaceutical composition" refers to a preparation of one or more of the active ingredients described herein, e.g. a construct encoding a human Beclin-1 variant, wherein threonine at position 119 of the human Beclin-1 variant is substituted with a phospho-mimicking residue, with other components such as physiologically suitable carriers and excipients. The purpose of a pharmaceutical composition is to facilitate administration of a compound to a subject.

Hereinafter, the phrases "therapeutically acceptable carrier" and "pharmaceutically acceptable carrier", which may be used interchangeably, refer to a carrier or a diluent that does not cause significant irritation to an organism and does not abrogate the biological activity and properties of the administered compound.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

In another embodiment of the present invention, a therapeutic composition further comprises a pharmaceutically acceptable carrier. As used herein, a "carrier" refers to any substance suitable as a vehicle for delivering a polynucleotide molecule of the present invention to a suitable in vivo or in vitro site. As such, carriers can act as a pharmaceutically acceptable excipient of a therapeutic composition containing a polynucleotide molecule of the present invention. Preferred carriers are capable of maintaining a polynucleotide molecule of the present invention in a form that, upon arrival of the polynucleotide molecule to a cell, the polynucleotide molecule is capable of entering the cell and being expressed by the cell. Carriers of the present invention include: (1) excipients or formularies that transport, but do not specifically target a nucleic acid molecule to a cell (referred to herein as non-targeting carriers); and (2) excipients or formularies that deliver a nucleic acid molecule to a specific site in a subject or a specific cell (i.e., targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- and o-cresol, formalin and benzol alcohol. Preferred auxiliary substances for aerosol delivery include surfactant substances non-toxic to a subject, for example, esters or partial esters of fatty acids containing from about six to about twenty-two carbon atoms. Examples of esters include: caproic, octanoic, lauric, palmitic, stearic, linoleic, linolenic, olesteric, and oleic acids. Other carriers can include metal particles (e.g., gold particles) for use with, for example, a biolistic gun through the skin. Therapeutic compositions of the present invention can be sterilized by conventional methods.

Targeting carriers are herein referred to as "delivery vehicles". Delivery vehicles of the present invention are capable of delivering a therapeutic composition of the present invention to a target site in a subject. A "target site" refers to a site in a subject to which one desires to deliver a therapeutic composition. Examples of delivery vehicles include, but are not limited to, artificial and natural lipid-containing delivery vehicles. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a nucleic acid molecule of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. For example, an antibody specific for an antigen found on the surface of a target cell can be introduced to the outer surface of a liposome delivery vehicle so as to target the delivery vehicle to the target cell. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

Preferably the pharmaceutical composition can also include a transfection agent such as DOTMA, DOPE, and DC-Chol (Tonkinson et al., 1996).

Another delivery vehicle comprises a recombinant virus particle. A recombinant virus particle of the present invention includes a therapeutic composition of the present invention, in which the recombinant molecules contained in the composition are packaged in a viral coat that allows entrance of DNA into a cell so that the DNA is expressed in the cell. A number of recombinant virus particles can be used, including, but not limited to, those based on adenoviruses, adeno-associated viruses, herpesviruses, lentivirus and retroviruses.

Other agents can be used are e.g. cationic lipids, polylysine, and dendrimers. Alternatively, naked DNA can be administered.

Therapeutic Use

According to some embodiments, the constructs, vectors and compositions of the invention are useful for the treatment of cancer, neurodegenerative diseases and other conditions in which inappropriate or detrimental expression of the human Beclin-1 and/or human DAPk gene is a component of the etiology or pathology of the condition, as detailed herein below.

Thus, some embodiments of the present invention are directed to the use of a recombinant construct that expresses in cells of a subject, a human Beclin-1 variant wherein threonine at position 119 of the human Beclin-1 variant is substituted with a phospho-mimicking residue, for the preparation of a medicament. In certain embodiments, the medicament is useful for treating or preventing a disorder associated with reduced or absence of expression of Beclin-1 and/or DAPk, for treating or preventing cancer, for inhibiting tumor progression or metastasis, for inducing tumor regression, preventing neurodegenerative diseases and/or inhibiting the progression of a degenerative disease.

According to another embodiment, the present invention provides a method for treating cancer or inhibiting tumor progression in a subject in need thereof comprising expressing in cells of the subject a human Beclin-1 variant of the invention thereby treating cancer in the subject and/or inhibiting tumor progression in a subject. According to one embodiment the expression of the human Beclin-1 variant in cells of the subject induces autophagy, thereby treating cancer or inhibiting tumor progression in the subject. According to another embodiment, the expression of the human Beclin-1 variant in cells of the subject induces cell death, thereby treating cancer or inhibiting tumor progression in the subject. According to another embodiment, the expression of the human Beclin-1 variant in cells of the subject restores cell growth control, thereby treating cancer or inhibiting tumor progression in the subject.

According to another embodiment, the method for treating cancer of inhibiting tumor progression comprises the administration of a therapeutically effective amount of a recombinant polynucleotide construct comprising the isolated polynucleotide encoding the human Beclin-1 variant of the present invention. According to another embodiment, the recombinant polynucleotide construct is administered into the subject's cells ex vivo.

According to another embodiment, the subject to be treated by methods and composition of the present invention is selected from the group consisting of a subject displaying pathology resulting from cancer, a subject suspected of displaying pathology resulting from cancer, and a subject at risk of displaying pathology resulting from cancer.

In one embodiment, the method comprises administering to said subject a recombinant construct comprising at least one polynucleotide sequence encoding a human Beclin-1 variant wherein threonine at position 119 of the human Beclin-1 variant is substituted with a phospho-mimicking residue, the nucleic acid sequence being operably linked to at least one transcription-regulating sequence.

Another aspect of the present invention is directed to a method for treating cancer in a subject in need thereof, comprising administering to the subject a therapeutically effective amount of a recombinant construct comprising at least one polynucleotide sequence encoding a human Beclin-1 variant wherein threonine at position 119 of the human Beclin-1 variant is substituted with a phospho-mimicking residue, the polynucleotide sequence being operably linked to at least one transcriptional initiation regulatory sequence, wherein said subject is afflicted with a tumor characterized by reduced or no expression of Beclin-1 in at least a portion of the cells of the tumor and/or reduced or no expression or activity of the death associated protein kinase (DAPk) in at least a portion of the cells of the tumor.

In another aspect, the invention provides a method for inhibiting tumor progression in a subject in need thereof, comprising administering to the subject a therapeutically effective amount of a recombinant construct comprising at least one polynucleotide sequence encoding a human Beclin-1 variant wherein threonine at position 119 of the human Beclin-1 variant is substituted with a phospho-mimicking residue, the polynucleotide sequence being operably linked to at least one transcriptional initiation regulatory sequence, wherein said subject is afflicted with a tumor characterized by reduced or no expression of Beclin-1 in at least a portion of the cells of the tumor and/or reduced or no expression or activity of the death associated protein kinase (DAPk) in at least a portion of the cells of the tumor.

In another aspect, there is provided a method for inducing tumor regression in a subject in need thereof, comprising administering to the subject a therapeutically effective amount of a recombinant construct comprising at least one nucleic acid sequence encoding a human Beclin-1 variant wherein threonine at position 119 of the human Beclin-1 variant is substituted with a phospho-mimicking residue, the polynucleotide sequence being operably linked to at least one transcriptional initiation regulatory sequence, wherein said subject is afflicted with a tumor characterized by reduced or no expression of Beclin-1 in at least a portion of the cells of the tumor and/or reduced or no expression or activity of the death associated protein kinase (DAPk) in at least a portion of the cells of the tumor.

In another embodiment, tumors that may be treated according to the method of the present invention are those characterized by reduced or no expression of Beclin-1 in at least a portion of the cells of the tumor and/or reduced or no expression or activity of the death associated protein kinase (DAPk) in at least a portion of the cells of the tumor. In another embodiment, the tumor is a solid tumor. For example, in some embodiments, the tumor may include pediatric solid tumors (e.g. Wilms' tumor, hepatoblastoma and embryonal rhabdomyosarcoma), wherein each possibility represents a separate embodiment of the present invention. In other embodiments, the tumor includes, but is not limited to, germ cell tumors and trophoblastic tumors (e.g. testicular germ cell tumors, immature teratoma of the ovary, sacrococcygeal tumors, choriocarcinoma and placental site trophoblastic tumors), wherein each possibility represents a separate embodiment of the present invention. According to additional embodiments, the tumor includes, but is not limited to, epithelial adult tumors (e.g. bladder carcinoma, hepatocellular carcinoma, ovarian carcinoma, cervical carcinoma, lung carcinoma, breast carcinoma, squamous cell carcinoma in head and neck, colon carcinoma, renal cell carcinoma and esophageal carcinoma), wherein each possibility represents a separate embodiment of the present invention. In yet further embodiments, the tumor includes, but is not limited to, neurogenic tumors (e.g. astrocytoma, ganglioblastoma and neuroblastoma), wherein each possibility represents a separate embodiment of the present invention. In another embodiment, the tumor is prostate cancer. In another embodiment, the tumor is pancreatic cancer. In other embodiments, the tumor includes, for example, Ewing sarcoma, congenital mesoblastic nephroma, gastric adenocarcinoma, parotid gland adenoid cystic carcinoma, duodenal adenocarcinoma, T-cell leukemia and lymphoma, nasopharyngeal angiofibroma, melanoma, osteosarcoma, uterus cancer and non-small cell lung carcinoma, wherein each possibility represents a separate embodiment of the present invention.

In certain embodiments, the polynucleotide constructs of the present invention can be used to treat cancer alone or in combination with other established or experimental therapeutic regimens against cancer. Therapeutic methods for treatment of cancer suitable for combination with the present invention include, but are not limited to, chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy, and photon beam radiosurgical therapy.

Screening

The present invention further provides a method of screening for a molecule that influences the intracellular concentration of human Beclin-1 phosphorylated at residue threonine 119, comprising:

(a) adding a putative molecule to a cell expressing human Beclin-1, (b) contacting the cell with an antibody of the invention under conditions such that a complex can form between phosphorylated Beclin-1 and the antibody and quantifying the amount of the complex formed, thereby quantifying the amount of phosphorylated Beclin-1 in the biological test sample; and (c) comparing the amount of phosphorylated Beclin-1 in the cell in the presence and absence of said putative molecule.

According to one embodiment, the putative molecule increases the intracellular concentration of the Thr119 phosphorylated human Beclin-1. According to another embodiment, the putative molecule decreases the intracellular concentration of the Thr119 phosphorylated human Beclin-1.

Having now generally described the invention, the same will be more readily understood through reference to the following examples, which are provided by way of illustration and are not intended to be limiting of the present invention.

SEQ ID #1
MEGSKTSNNSTMQVSFVCQRCSQPLKLDTSFKILDRVTIQELTAPLLT

TAQAKPGETQEEETNSGEEPFIETPRQDGVSRRFIPPARMMSTESANS

FTLIGEVSDGGTMENLSRRLKV<u>T</u>GDLFDIMSGQTDVDHPLCEECTDTL

LDQLDTQLNVTENECQNYKRCLEILEQMNEDDSEQLQMELKELALEEE

RLIQELEDVEKNRKIVAENLEKVQAEAERLDQEEAQYQREYSEFKRQQ

LELDDELKSVENQMRYAQTQLDKLKKTNVFNATFHIWHSGQFGTINNF

RLGRLPSVPVEWNEINAAWGQTVLLLHALANKMGLKFQRYRLVPYGNH

SYLESLTDKSKELPLYCSGGLRFFWDNKFDHAMVAFLDCVQQFKEEVE

KGETRFCLPYRMDVEKGKIEDTGGSGGSYSIKTQFNSEEQWTKALKFM

LTNLKWGLAWVSSQFYNK

-continued

SEQ ID #2
MEGSKTSNNSTMQVSFVCQRCSQPLKLDTSFKILDRVTIQELTAPLLT

TAQAKPGETQEEETNSGEEPFIETPRQDGVSRRFIPPARMMSTESANS

FTLIGEVSDGGTMENLSRRLKVEGDLFDIMSGQTDVDHPLCEECTDTL

LDQLDTQLNVTENECQNYKRCLEILEQMNEDDSEQLQMELKELALEEE

RLIQELEDVEKNRKIVAENLEKVQAEAERLDQEEAQYQREYSEFKRQQ

LELDDELKSVENQMRYAQTQLDKLKKTNVFNATFHIWHSGQFGTINNF

RLGRLPSVPVEWNEINAAWGQTVLLLHALANKMGLKFQRYRLVPYGNH

SYLESLTDKSKELPLYCSGGLRFFWDNKFDHAMVAFLDCVQQFKEEVE

KGETRFCLPYRMDVEKGKIEDTGGSGGSYSIKTQFNSEEQWTKALKFM

LTNLKWGLAWVSSQFYNK

SEQ ID #3
MEGSKTSNNSTMQVSFVCQRCSQPLKLDTSFKILDRVTIQELTAPLLT

TAQAKPGETQEEETNSGEEPFIETPRQDGVSRRFIPPARMMSTESANS

FTLIGEVSDGGTMENLSRRLKVDGDLFDIMSGQTDVDHPLCEECTDTL

LDQLDTQLNVTENECQNYKRCLEILEQMNEDDSEQLQMELKELALEEE

RLIQELEDVEKNRKIVAENLEKVQAEAERLDQEEAQYQREYSEFKRQQ

LELDDELKSVENQMRYAQTQLDKLKKTNVFNATFHIWHSGQFGTINNF

RLGRLPSVPVEWNEINAAWGQTVLLLHALANKMGLKFQRYRLVPYGNH

SYLESLTDKSKELPLYCSGGLRFFWDNKFDHAMVAFLDCVQQFKEEVE

KGETRFCLPYRMDVEKGKIEDTGGSGGSYSIKTQFNSEEQWTKALKFM

LTNLKWGLAWVSSQFYNK

SEQ ID #4
MEGSKTSNNSTMQVSFVCQRCSQPLKLDTSFKILDRVTIQELTAPLLT

TAQAKPGETQEEETNSGEEPFIETPRQDGVSRRFIPPARMMSTESANS

FTLIGEVSDGGTMENLSRRLKVAGDLFDIMSGQTDVDHPLCEECTDTL

LDQLDTQLNVTENECQNYKRCLEILEQMNEDDSEQLQMELKELALEEE

RLIQELEDVEKNRKIVAENLEKVQAEAERLDQEEAQYQREYSEFKRQQ

LELDDELKSVENQMRYAQTQLDKLKKTNVFNATFHIWHSGQFGTINNF

RLGRLPSVPVEWNEINAAWGQTVLLLHALANKMGLKFQRYRLVPYGNH

SYLESLTDKSKELPLYCSGGLRFFWDNKFDHAMVAFLDCVQQFKEEVE

KGETRFCLPYRMDVEKGKIEDTGGSGGSYSIKTQFNSEEQWTKALKFM

LTNLKWGLAWVSSQFYNK

EXAMPLES

Methods

Cell Cultures and Co-Immunoprecipitations

HEK293 cells were grown in DMEM medium (Biological Industries) supplemented with glutamine, penicillin and streptomycin (Gibco BRL), and 10% fetal bovine serum (Hyclone). Cells were transiently transfected by the standard calcium phosphate technique with the indicated plasmids. Cell pellets were lysed in NP-40 buffer or in B buffer (supplementary information) supplemented with 1 mM $Na_3VO_4$, 1 mM DTT, and protease inhibitors. When the phosphorylation state of Beclin-1 was examined 1 mM NaF and 50 mM β-glycerolphosphate were added. Following pre-clearance with protein G PLUS-Agarose beads (Santa Cruz Biotechnology), the extracts were incubated with anti-Flag M2 beads (Sigma) for 2 hours, eluted with excess Flag peptide (Sigma), and subjected to western blot analysis.

GFP-LC3 Punctate Staining Assay

HEK293 cells were plated in 9 cm plates containing poly-Lysine-covered 13 mm glass cover slips, and after 24 hrs the cells were transfected as indicated below. At different time points post-transfection the cells grown on the cover slips were fixed with 3.7% formaldehyde, and the rest of the cells were extracted using PLB buffer (supplementary information) containing protease inhibitors, and subjected to western blot analysis. To visualize autophagosomes, fixed cells were viewed by fluorescent microscopy (Olympus BX41) with 60× (N.A. 1.25) UPlan-F1 oil immersion objectives, and digital images obtained with a DP50 CCD camera using cell^A software (Olympus). The percentage of cells with punctate GFP-LC3 fluorescence (more than 5 puncta/cell) per total GFP-LC3-positive cells (n=100) was quantified.

In FIG. 1, the cells were transfected with pSUPER-based shRNAs targeting Beclin-1 or the fluorescence protein HcRed as a negative control (Reef et al., 2006) together with GFP-LC3 plasmid and DAPk ΔCaM or pcDNA3 vector expressing luciferase (LUC). Cells were fixed 72 hrs post-transfection.

To assess the function of the phosphorylation mutants (FIG. 5C), the cells were transfected with 5 or 10 μg T119A or T119E Beclin-1 mutants together with GFP-LC3 plasmid. Cells were fixed 24 hrs post-transfection.

Structure Analysis

Figure 4A:
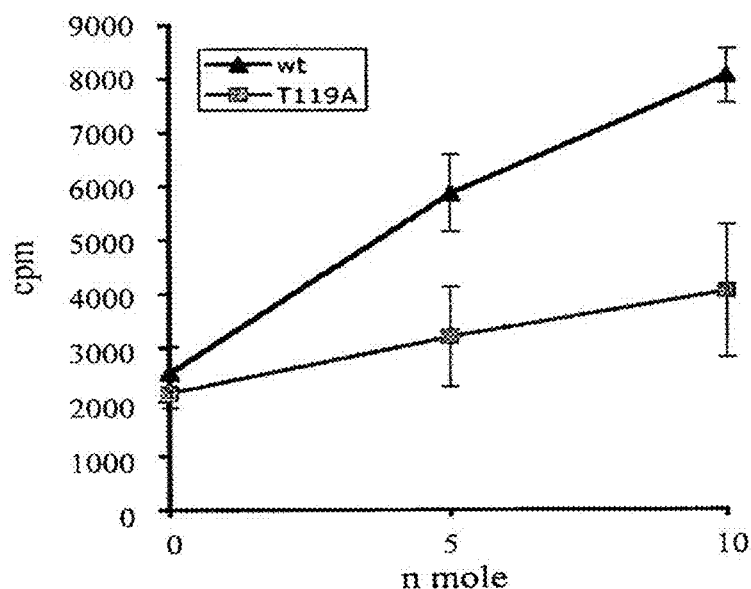
FIG. 4: DAPk phosphorylates Beclin-1 on Thr119 located within its BH3 domain. (A) DAPk phosphorylates Beclin's BH3 peptide in a dose-dependent manner. Data are the mean±SD of three different experiments (B) A model of the interaction between Beclin's BH3 domain, and Bcl-$X_L$'s hydrophobic pocket. (C) Phosphorylation on Thr119 detected by an anti-phospho Thr119 antibody (Western blot); total GST-Beclin-1 levels were visualized by Ponceau S staining. (D) DAPk phosphorylates Beclin-1 purified from mammalian cell in vitro on Thr119. Phosphorylated proteins were visualized by X-ray film exposure. The phosphorylation on Thr119 was visualized by western blot analysis using anti phospho Thr119 Beclin-1 antibodies. (E) Phosphorylation of Beclin-1 by DAPk in HEK293 cells transfected with ΔCaM DAPk strongly increased the phosphorylation state of Beclin-1.
Figure 4B:
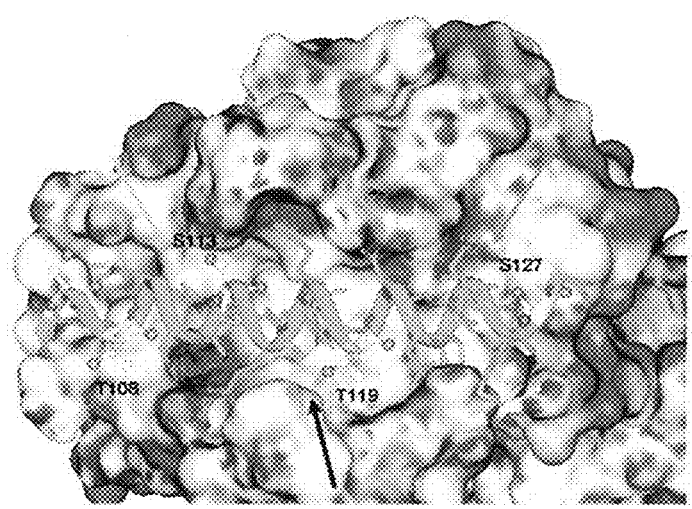

The structure analysis was based on the X-ray structure of Bcl-$X_L$ in complex with Beclin-1, taken from the Protein Data Bank (Berman et al., 2000) entry 2 μl. FIG. 4B was prepared with the program InsightII (Accelrys Inc. San-Diego, Calif.); the electrostatic potential was calculated using the Delphi module of InsightII.

DNA Constructs, Buffers and Antibodies

The following DNA plasmids were used: HA-DAPk, HA-ΔCaM DAPk (Cohen et al., 1997, *EMBO J.*, 16, 998-1008), Flag-Beclin-1 or Flag-Beclin-1 ΔBcl-2 binding domain, Bcl-XL, GST, and GST-Beclin-1. The threonine substitutions in the GST-Beclin-1 T119A, Flag-Beclin-1 T119A and Flag-Beclin-1 T119E were generated by site-directed mutagenesis (QuikChange Site-Directed Mutagenesis Kit, Stratagene).

The following antibodies were used: monoclonal antibodies to actin, DAPk, Flag (Sigma), to Bcl-2 (Santa Cruz Biotechnology), or to HA (BAbCO). HRP-conjugated goat anti-mouse, or anti-rabbit secondary antibodies (Jackson Immuno-Research), were used as required. Antibodies were visualized by enhanced chemiluminescence (Supersignal; Pierce) according to the manufacturer's instructions.

The following buffers were used: B buffer (0.4% NP-40, 0.5 mM EDTA, 100 mM KCl, 20 mM Hepes pH-7.6 and 20% glycerol), NP-40 buffer (300 mM NaCl, 10 mM Tris pH-7.4, and 0.5% NP-40). PLB buffer (100 mM NaCl, 10 mM $NaPO_4$, 5 mM EDTA pH 8.0, 1% Triton X-100, 0.5% sodium deoxycholate and 0.1% SDS).

Pull-Down Assay

COS7 cells or HEK293T cells were washed once with ice-cold phosphate buffered saline, and lysed in 600 ml CHAPS solubilization buffer (20 mM Tris pH-7.5, 5 mM EDTA, 5 mM EGTA, 100 mM NaCl, 1% CHAPS) supplemented with 0.2 mM $Na_3VO_4$ and protease inhibitors. Soluble extracts were prepared by centrifugation at 14,000 g for 10 min at 4° C. Beclin-1 interacting proteins were precipitated from the cell lysates at 4° C. for 2 hours, using GST-Beclin-1 fusion protein conjugated to glutathione agarose beads. GST protein conjugated to glutathione agarose beads were used as a negative control. Beads were collected by centrifugation, washed with the lysis buffer and re-suspended in protein sample buffer. Proteins were separated by 10% SDS-PAGE, and blotted onto nitrocellulose membranes which were incubated with the indicated antibodies.

In Vitro Kinase Assay

HEK293T cells were transiently transfected by the standard calcium phosphate technique with full length Flag-DAPk or Flag-tagged Beclin-1. After 24 hours cell pellets were lysed in B buffer, supplemented with protease inhibitors, and with 1 mM NaF and 50 mM β-glycerolphosphate. Extracts were immunoprecipitated with anti-Flag M2 beads (Sigma), and proteins were eluted with excess Flag peptide. When high salt concentration was used, Beclin-1-bound beads were first washed stringently in 0.5 M LiCl followed by 0.5 M KCl to remove co-immunoprecipitating kinases. For in vitro kinase assays, full length DAPk and Flag-tagged Beclin-1 or bacterially purified GST/GST-Beclin-1 were used as indicated in the figure legends, and were incubated at 30° C. in kinase buffer (50 mM Hepes pH 7.5, 20 mM $MgCl_2$) supplemented with 0.116 µCi/µl [γ-33P]ATP, 50 µM ATP, 1 µM bovine calmodulin, and 0.2 mM $CaCl_2$. Reactions were terminated by boiling in SDS-loading buffer, and were resolved on 10% polyacrylamide gels, blotted onto nitrocellulose membranes, and exposed to MR X-ray film (Kodak).

For peptide phosphorylation, DAPk's catalytic domain (DK1) was expressed in TOP10 bacteria (Invitrogen) upon induction with tetracycline, and affinity purified from bacterial lysates using the StrepTactin column (Genosys Biotechnologies) according to the manufacturer's instructions. A peptide corresponding to Beclin's BH3 domain (aa 108-127) was synthesized as well as the same peptide where Thr119 was substituted to alanine, and used in P-81 Whatman filter assays. DK1 (8 ng) was incubated for 15 min at 30° C. with increasing concentrations of peptide (5-50 nmoles) in reaction buffer of 50 mM Hepes, pH 7.5, 20 mM MgCl2, 133 mM ATP and 4 mCi [γ-33P]ATP. Reactions were applied to P-81 filters and washed extensively in 1% phosphoric acid. Total counts were measured by scintillation counting.

Transmission Electron Microscopy

HEK293 cells were transfected with Flag-Beclin, Bcl-XL, and with DAPk ΔCaM or pcDNA3-luciferase plasmids After 24 hrs the cells were fixed for 1 hour in Karnovsky's fixative (3% paraformaldehyde, 2% glutaraldehyde, 5 mM $CaCl_2$ in 0.1 M cacodylate buffer, pH 7.4, containing 3% sucrose). Cells were harvested and embedded with agar noble to a final concentration of 1.7% and post fixed with 1% $OsO_4$, 0.5% potassium dichromate and 0.5% potassium hexacyanoferrate in 0.1 M cacodylate buffer. The pellet was stained and blocked with 2% aqueous uranyl acetate followed by ethanol dehydration, and embedded in graded Epon 812. Ultrathin sections (70-90 nm thickness) were sectioned with Ultramicrotome Leica UCT, analyzed under 120 kV at Tecnai 12 Transmission Electron Microscope (TEM) and imaged with Eagle 2 k×2 k CCD camera FEI (Eindhoven Netherlands).

In Gel Proteolysis and Mass Spectrometry Analysis

For in vitro kinase assays, 60 ng Flag-tagged DAPk and 1050 ng bacterially purified GST-Beclin-1 were incubated at 30° C. in kinase buffer (50 mM Hepes pH 7.5, mM $MgCl_2$) supplemented with 500 µM ATP, 1 µM bovine calmodulin, and 0.2 mM $CaCl_2$. After 2 hours 60 ng DAPk were added to the reaction mix and the reactions were terminated 2 hours later by boiling in SDS-loading buffer, and were resolved on 10% acrylamide gels.

The proteins in the gel were reduced (10 mM DTT), modified with 40 mM iodoacetamide and proteolyzed (modified trypsin or chymotrypsin (Promega)) at a 1:100 enzyme-to-substrate ratio. The resulting peptides were resolved by reversephase chromatography on 0.075×200-mm fused silica capillaries (J&W) packed with Reprosil reversed phase material (Dr Maisch GmbH, Germany). The peptides were eluted with linear 90 minutes gradients of 5 to 45% and 15 minutes at 95% acetonitrile with 0.1% formic acid in water at flow rates of 0.25 µl/min. Mass spectrometry was performed by an ion-trap mass spectrometer (Orbitrap, Thermo) in a positive mode using repetitively full MS scan followed by collision induces dissociation (CID) of the 7 most dominant ion selected from the first MS scan. $Fe^{+2}$ columns (Sigma) were used to enrich phosphopeptides (binding in 250 mM acetic acid, 30% acetonitrile and elution in 400 mM ammonium hydroxide).

These peptides were analyzed similarly except the usage of multistage activation in the fragmentation method. The mass spectrometry data was analyzed using the Sequest 3.31 software (J. Eng and J. Yates, University of Washington and Finnigan, San Jose) and Pep-Miner (Beer et al., 2004, *Proteomics*, 4, 950-60) searching against the human part of the NCBI-NR database.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

Example 1

Functional Interactions Between DAPk and Beclin-1

To address the molecular mechanisms through which DAPk promotes autophagy we focused on the early steps of vesicle nucleation in which Beclin-1 participates. We first tested whether the knock-down of Beclin-1 inhibits DAPk-induced autophagy by co-transfecting HEK293 cells with ΔCaM DAPk (activated form of DAPk lacking its calmodulin (CaM)-regulatory domain; (Cohen et al., 1997, *EMBO J.*, 16, 998-1008)) and shRNA plasmid targeting Beclin-1. A third co-transfected construct was GFP-LC3 used to assess the autophagy process by scoring LC3 punctate staining (Kabeya et al., 2000, *EMBO J.*, 19, 5720-8). As a control vector, we used pcDNA3-luciferase (LUC), together with shRNAs targeting Beclin-1 or HcRed, and with the GFP-LC3 plasmid. After 72 hours cells were counted and lysates were prepared and the percentage of cells with punctate GFP-LC3 fluorescence per total GFP-LC3-positive cells was quantified. The frequency of cells in which the GFP-LC3 appeared in puncta increased over basal levels when ΔCaM DAPk was introduced to the cells (FIGS. 1A, 1B, 1C and 1D) and was significantly reduced by knocking down Beclin-1 (FIG. 1A). These results indicate that Beclin-1 is required for DAPk-induced autophagy.

Example 2

Beclin-1 is a Novel Substrate of DAPk

Figure 2A:
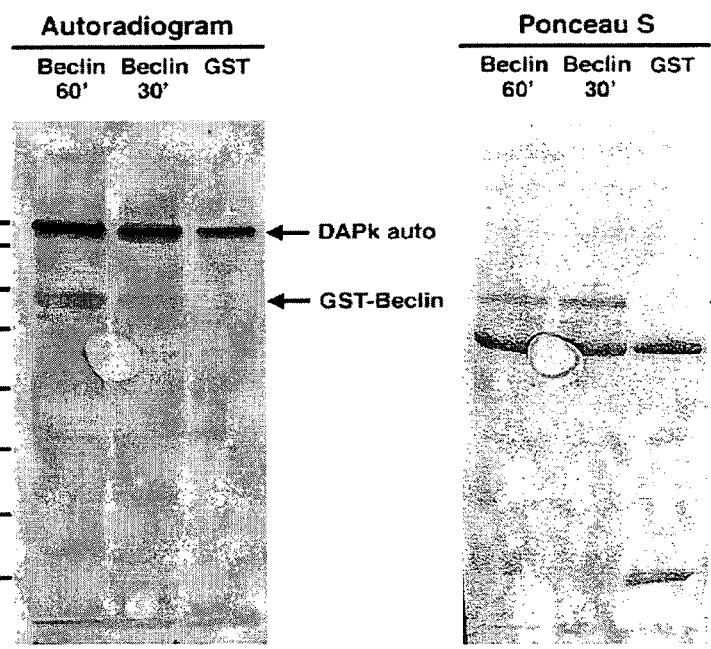
FIG. 2 A-C: Beclin-1 is a novel substrate of DAPk: (A-B) GST-Beclin-1, but not GST alone was phosphorylated by DAPk after incubation for 30 and 60 min with various amounts of DAPk, GST and GST-Beclin-1 (the numbers indicated in the figure are the amount of protein used in ng). Phosphorylated proteins were visualized by X-ray film exposure, and GST/GST-Beclin-1 levels were visualized by Ponceau S staining. (C) Flag-Tagged DAPk phosphorylates Flag-tagged Beclin-1 purified from HEK293T cells. Where indicated (+LiCl), Beclin-1-bound beads were first washed stringently in 0.5 M LiCl and 0.5 M KCl. Phosphorylated proteins were visualized by X-ray film exposure, and Beclin-1's levels were visualized by western blot analysis using anti-Beclin-1 antibodies.
Figure 2B:
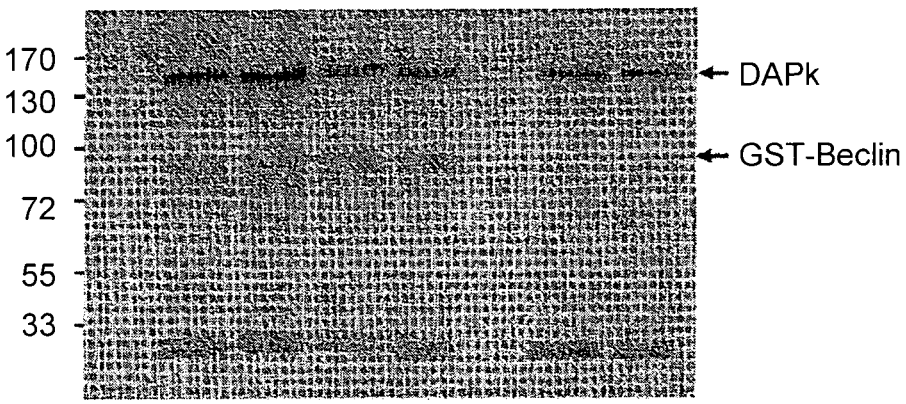
Figure 2C:
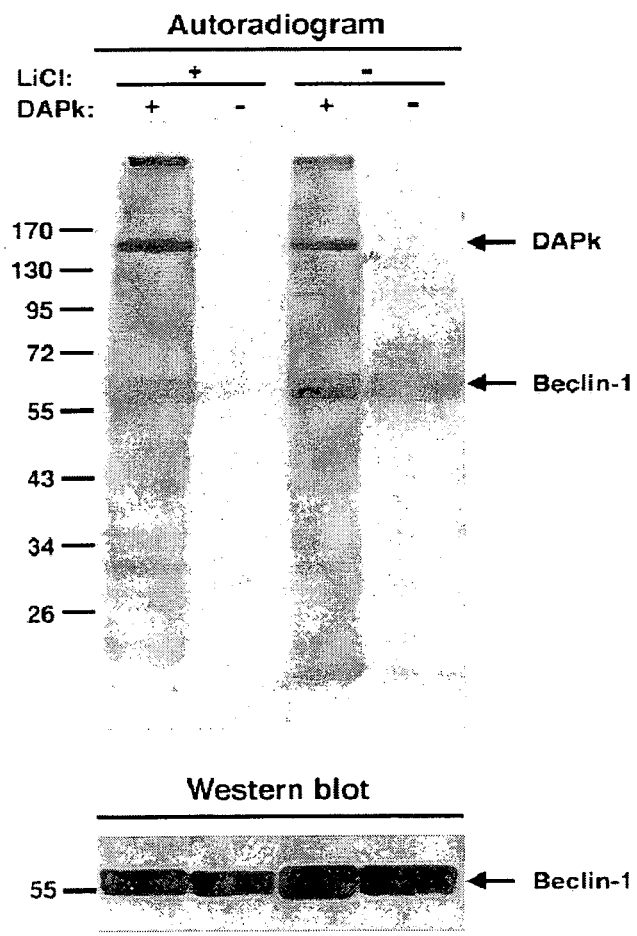

We examined if DAPk phosphorylates Beclin-1 by in vitro kinase assays in which purified Flag tagged DAPk (100 ng) was incubated with GST-Beclin-1 (750 ng) in the presence of $Ca^{2+}$, calmodulin and $[\gamma^{-33}P]$ ATP for 30 min or 60 min. Phosphorylated proteins were visualized by X-ray film exposure, and GST/GST-Beclin-1 levels were visualized by Ponceau S staining. GST-Beclin-1, but not GST alone, was phosphorylated by DAPk (FIG. 2A). The autophosphorylation of DAPk indicates that DAPk was active in all samples. The phosphorylation by Flag-tagged (60 ng) DAPk was also observed when Flag-tagged Beclin-1 (250 ng), immunoprecipitated from HEK293T cells, was used as a substrate and a kinase assay was performed for 60 min (FIG. 2B). In this context Beclin-1 pulled down endogenous kinase(s) which induced some background phosphorylation without adding external DAPk (FIG. 2B-*right* lane). The latter was prevented by washing the Beclin-1 immunoprecipitates with high salt concentrations (i.e., 0.5M KCl and LiCl) prior to the kinase assay (FIG. 2B-*left* two lanes). Together, these results indicate that DAPk phosphorylates Beclin-1 purified from bacterial or mammalian cells.

Figure 3A:
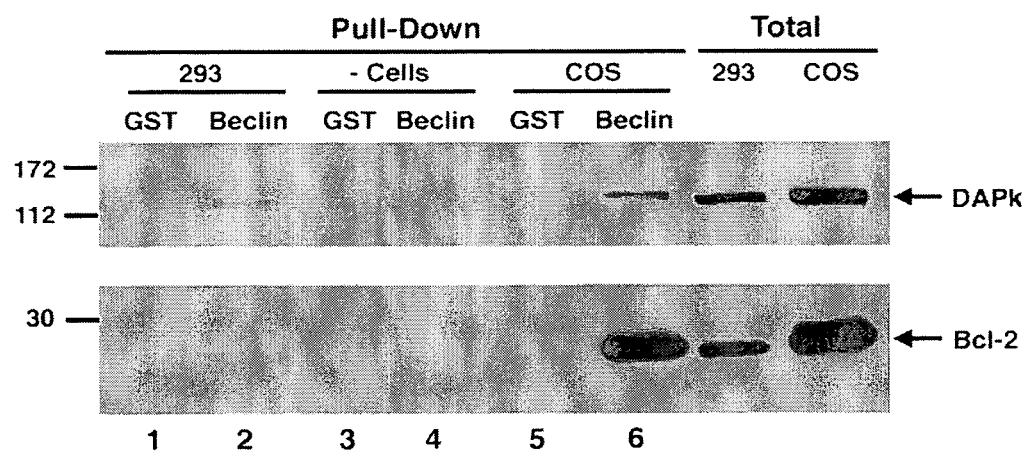
FIG. 3: Physical interaction between DAPk and Beclin-1: (A) GST-Beclin-1, but not GST alone pulled down the endogenous DAPk when added to protein extracts from COST cells and HEK293T cells. (B) Ponceau S staining of GST/GST-Beclin-1 to which the extracts were added. (C) Beclin-1 lacking the Bcl-2 binding domain (ΔBD) does not bind DAPk. (D) Beclin-1 immunoprecipitated the endogenous DAPk from HEK293T cells.
Figure 3B:
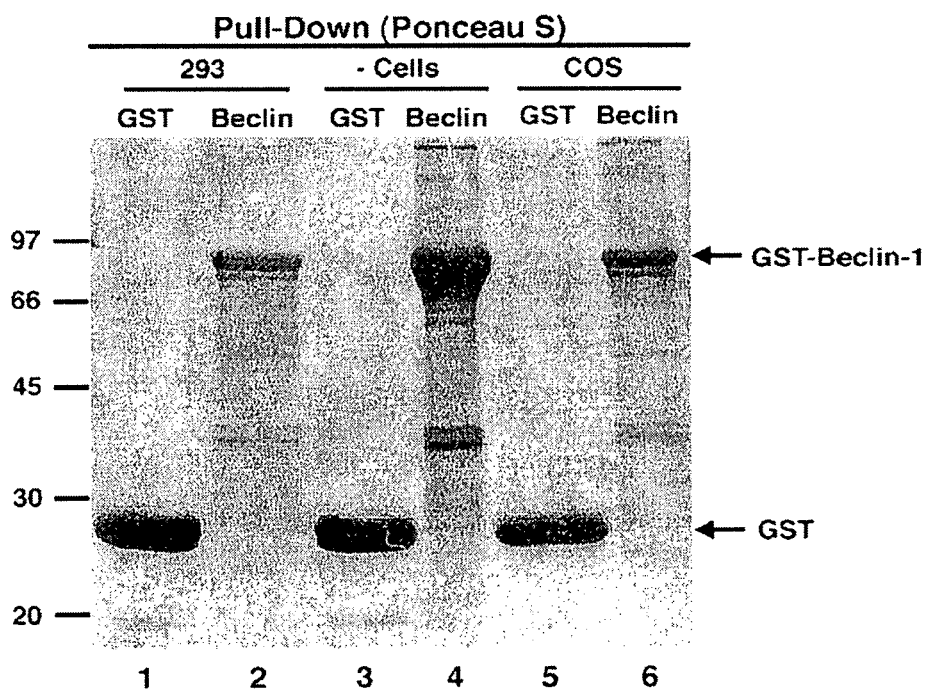
Figure 3C:
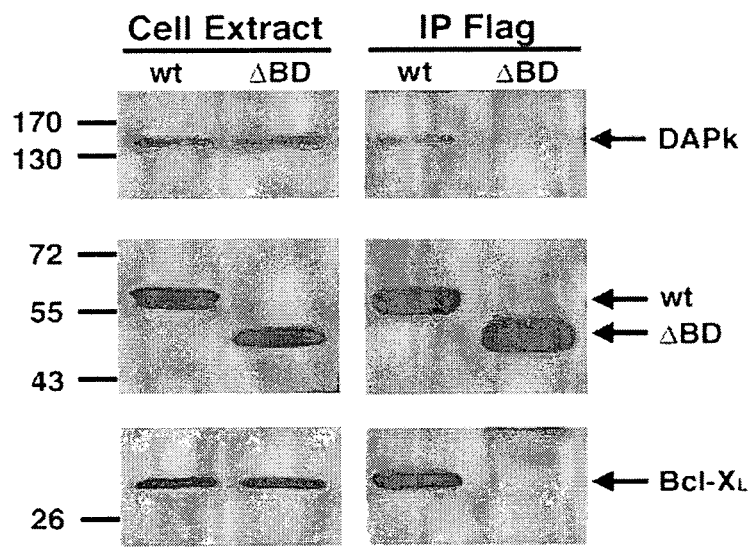
Figure 3D:
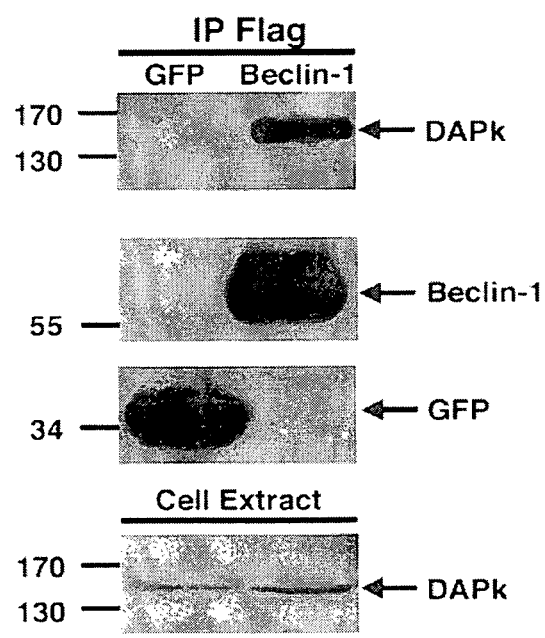

The existence of physical interactions between the two proteins was first documented by showing that GST-Beclin-1, but not GST alone, pulled down the endogenous DAPk when added to protein extracts from COST cells or HEK293T cells. As expected, Bcl-2 was pulled down as well (FIG. 3A). In a second set of experiments, Flag-tagged Beclin-1 and HA-tagged DAPk were co-expressed in HEK293 cells, Beclin-1 was immunoprecipitated with anti-Flag antibodies, and eluted from the beads by Flag peptide. Over-expressed Bcl-$X_L$ was used as a positive control. It was found that Beclin-1 binds the HA-tagged DAPk (FIG. 3B wt). Notably, the Flag-tagged Beclin-1 also immunoprecipitated the endogenous DAPk from HEK293T cells (FIG. 3C). Interestingly, when Beclin-1 lacking the Bcl-2 binding domain (i.e., aa 88-150) was immunoprecipitated, DAPk could no longer bind Beclin-1 (FIG. 3B, ΔBD). Thus, the results imply that DAPk binds to Beclin-1, and that the Bcl-2 binding domain is required for this interaction.

Example 3

DAPk Phosphorylates Beclin-1 on its BH3 Domain

In light of our finding that the interaction of DAPk with Beclin-1 depends on the presence of the Bcl-2 binding domain, we studied if DAPk phosphorylates Beclin-1 on this region, and more specifically on its BH3 domain. Bacterially-purified DAPk's catalytic domain was incubated for 15 min at 30° C. with increasing concentrations (5-50 nmoles) of a peptide corresponding to Beclin's BH3 domain (aa 108-127) as well as with the same peptide where Thr119 was substituted to alanine. In vitro kinase assay was performed, and the reactions were applied to Whatman filters. Total levels of TCA insoluble counts were measured and plotted against substrate concentration. It was found that DAPk phosphorylates Beclin's BH3 peptide in a dose-dependent manner (FIG. 4A).

Next we examined the available crystal structure of the Bcl-$X_L$/Beclin-1 complex (Oberstein et al., 2007, *J. Biol. Chem.*, 282, 13123-32) in attempt to predict in silico which Ser/Thr residues in Beclin-1's BH3 domain might affect the interaction with Bcl-$X_L$ upon its phosphorylation. Specifically we examined each of the four Ser/Thr residues (T108, S113, T119, S127) located within Beclin's BH3 domain (FIG. 4B). T108 is partially buried with its Cβ2 atom interacting with L112 of Bcl-$X_L$, and its Oγ1 atom exposed to the solvent. Phosphorylation at this site will not cause steric clash as the $PO_3$ group will point towards the solvent. S113 binds in a shallow pocket of Bcl-$X_L$. Phosphorylation on this residue is not likely to have a severe influence because the $PO_3$ group can be accommodated in a groove next to the S113 binding pocket. T119 is partially buried. Its Cγ atom makes a hydrophobic contact with F97 of Bcl-$X_L$ whereas its Oγ atom makes a hydrogen bond with the backbone carbonyl of Beclin-1 R115. Phosphorylation on this residue is likely to cause a severe clash with Bcl-$X_L$, and possibly disrupt the Beclin-1 helix. 5127 is partially buried. Its Oγ atom makes a hydrogen bond with the hydroxyloxygen of Bcl-$X_L$ Y195. Phosphorylation at this position will require a minor conformation change (rotation of S 127 about χ1) in order to accommodate the $PO_3$ group in a positively charged groove; the hydrogen bond with Y195 will however be disrupted. Y195 of Bcl-$X_L$ makes another hydrogen bond with Beclin-1 D124, which will not be affected by the phosphorylation of S127. Based on this analysis we concluded that phosphorylation on T119 may disrupt the binding of Beclin-1 to Bcl-$X_L$ and therefore is a potential target to DAPk.

A mutant BH3 peptide in which Thr119 was substituted to alanine (T119A) was synthesized, and its phosphorylation compared to the wt peptide. Changing Thr119 to alanine strongly inhibited the extent of peptide phosphorylation (FIG. 4A). Notably, this substitution did not abolish completely the phosphorylation, and some residual radioactivity was still incorporated into the peptide suggesting that other Ser/Thr sites may be weakly phosphorylated under the conditions used. These experimental data point at Thr119 as a major target for phosphorylation by DAPk.

Next, the full length GST-Beclin-1 protein was incubated with DAPk and cold ATP, proteolyzed and analyzed by mass spectrometry in order to map the phosphorylation site/s. Around 76% of Beclin-1's amino acids were covered in this analysis, out of which two phosphorylation sites were identified with good accuracy, both of which are located within the BH3 domain. The first was located in peptide 103-118, where the fragmentation data could not differ between a phosphorylation on S104 or T108, and the second was identified as Thr119. Thus, the phosphopeptide mapping confirmed that DAPk phosphorylates Beclin-1 on Thr119.

Example 4

Anti-Phospho Thr119 Antibodies Indicate that DAPk Phosphorylates Beclin-1 on its BH3 Domain Anti-phospho Thr119 antibodies were generated as follows: Rabbits were immunized with a synthetic phosphorylated peptide corresponding to amino acids 115-123 (pThr 119) of human Beclin-1, conjugated to KLH. The specific antibody was purified by first negatively absorbing, the antiserum on the corresponding non-phosphorylated Beclin-1 peptide, to remove undesired antibodies to non-phosphorylated Beclin-1, and then affinity-purifying the non-absorbed fraction using the immunizing phosphorylated peptide immobilized on agarose.

Figure 4C:
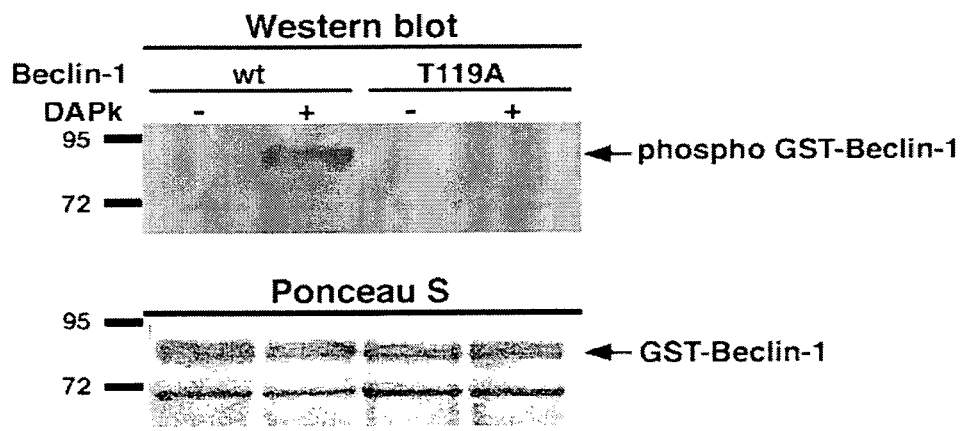
Figure 4D:
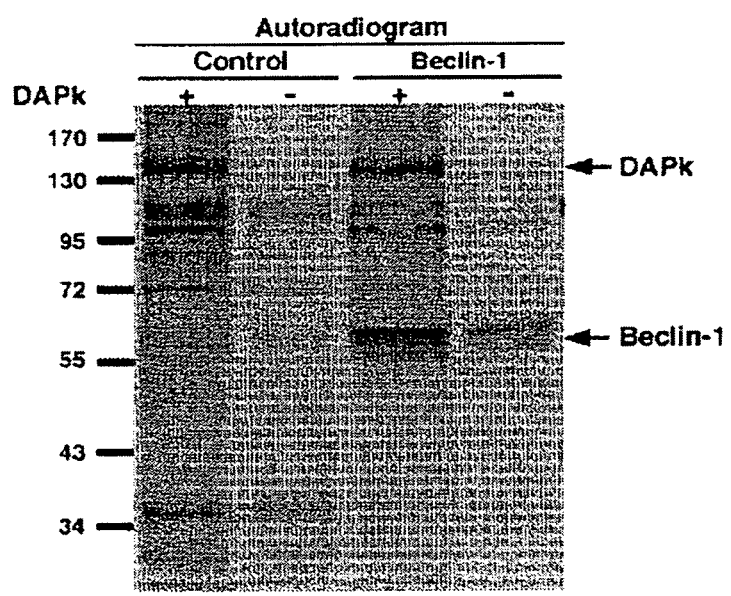
Figure 4D:
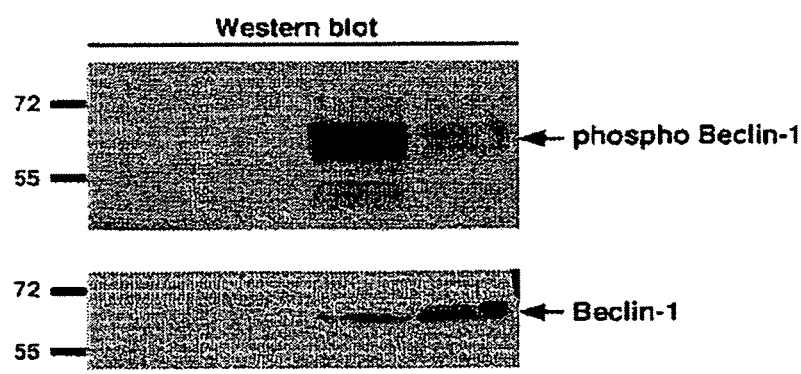
Figure 4E:
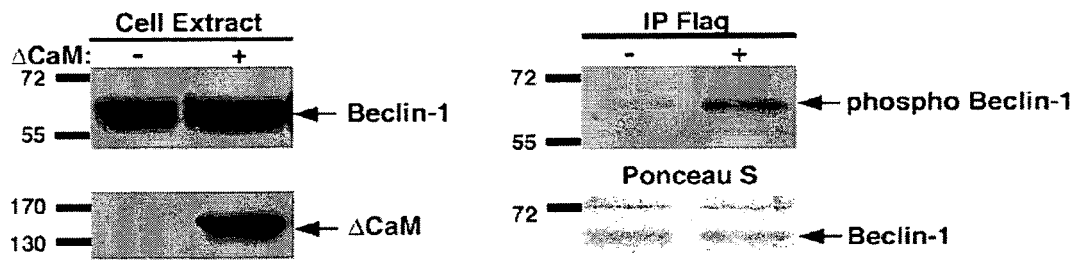

Anti-phospho Thr119 antibodies were tested against GST-Beclin-1 subjected to in vitro kinase assay with DAPk (Flag tagged DAPk (60 ng) was incubated with GST-wt Beclin-1 or with GST-T119A Beclin-1 (1000 ng) in the presence of $Ca^{2+}$, calmodulin and ATP for 30 min). These antibodies exclusively recognized the in vitro phosphorylated Beclin-1 (FIG. 4C, wt). Moreover, when a mutant GST-Beclin-1 in which Thr119 was substituted to alanine (T119A) was used, the antibodies could no longer detect DAPk-mediated phosphorylation (FIG. 4C, T119A), confirming the specificity of these antibodies, and proving that Thr119 residue is phosphorylated by DAPk. Similar results were obtained when Flag-tagged Beclin-1, immunoprecipitated from mammalian cells, was incubated with DAPk Flag-Tagged DAPk (60 ng) was incubated with Flag-tagged Beclin-1 (300 ng) purified from HEK293T cells by anti Flag antibodies and eluted from the beads by excess of Flag peptide. The kinase assay was performed for 30 min. Eluates obtained from similar amounts of untransfected cells which went through the same purification procedure as the cell lysates prepared from the Beclin-1 transfected cells, were incubated with DAPk as a control. Phosphorylated proteins were visualized by X-ray film exposure (autoradiogram). After the radioactivity on the blots decayed, the phosphorylation on Thr119 was visualized by western blot analysis using anti-phospho Thr119 Beclin-1 antibodies (Western blot, FIG. 4D upper panel). Total amount of eluted Beclin-1 was visualized by anti-Flag antibodies (Western blot, FIG. 4D lower panel). Interestingly these antibodies also recognized the background phosphorylation caused by the endogenous kinase(s) which co-immunoprecipitated with Beclin-1-FIG. 4D right lane). Anti-phospho Thr119 antibodies were then used for detecting the phosphorylation of Beclin-1 by DAPk in cells. HEK293 cells were co-transfected with Flag-tagged Beclin-1 with or without ΔCaM DAPk. After 24 hours Beclin-1 was immunoprecipitated from cells, using anti-Flag antibodies, and the immunoprecipitates were reacted with anti-phospho Thr119 antibodies. The ponceau staining shows equal amounts of immunoprecipitated Beclin-1. The cell extract blots were reacted with anti HA antibodies or with anti Beclin-1 antibodies. Transfection of HEK293 cells with ΔCaM DAPk strongly increased the phosphorylation state of Beclin-1 (FIG. 4E) indicating that phosphorylation on Thr119 occurs by DAPk in cells.

Altogether the peptide phosphorylation assays, the phospho-peptide mapping by mass-spectrometry, and the use of the anti phospho Thr119 antibodies establish that Thr119 within Beclin-1's BH3 domain, is specifically phosphorylated by DAPk.

Example 5

DAPk Promotes Beclin's Dissociation from Bcl-$X_L$

Figure 5A:
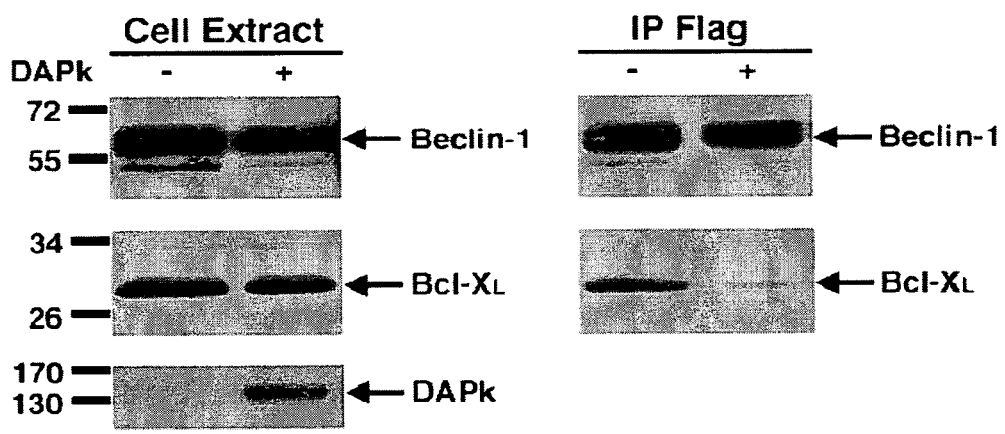
FIG. 5: DAPk promotes Beclin's dissociation from Bcl-$X_L$. (A) The levels of Bcl-$X_L$ co-immunoprecipitated with Beclin-1 are significantly reduced in HEK293 cells transfected with DAPk. (B) The levels of Bcl-$X_L$ co-immunoprecipitated with Beclin-1 are significantly reduced in HEK293 cells transfected with ΔCaM DAPk. (C) A phospho-mimicking mutant of Beclin-1 (T119E) strongly reduces the binding to Bcl-$X_L$. (D) T119E and T119A are expressed to the same extent in HEK293 cells; (E-F) Phosphorylation on Thr119 is causing Beclin's dissociation from Bcl-$X_L$, leading to increased autophagosome. The frequency of cells in which GFP-LC3 appeared in puncta increased in a dose dependent manner only when Beclin-1 T119E was induced to the cells. Data presented are the mean±SD from triplicates of 100 transfected cells. Single asterisk denotes significance level of $p<0.01$, and double asterisks denote significance of $p<0.005$. (G) Lack of phosphorylation at position Thr119 (T119A) leads to a stronger interaction between Beclin-1 and Bcl-$X_L$ which becomes resistant to DAPk (ΔCaM DAPk) dissociating effects; (H-K) Transmission electron micrographs of HEK293 cells 24 hours after they were transfected with Bcl-$X_L$, Flag-tagged Beclin-1 and ΔCaM (1-K) or pcDNA3-luciferase as a control (H). a(J) and (K) were taken at higher magnification of the ΔCaM treatment, (see the scale bar). "AV" indicates autophagic vacuoles.
Figure 5B:
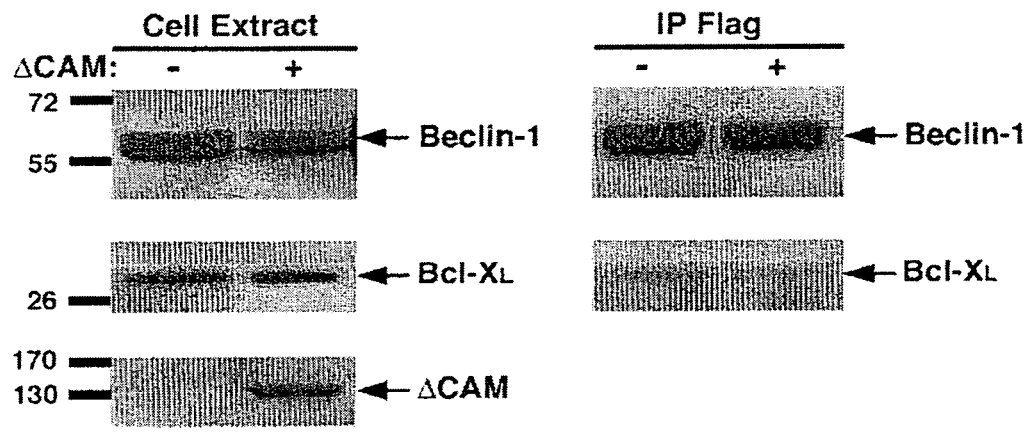
Figure 5C:
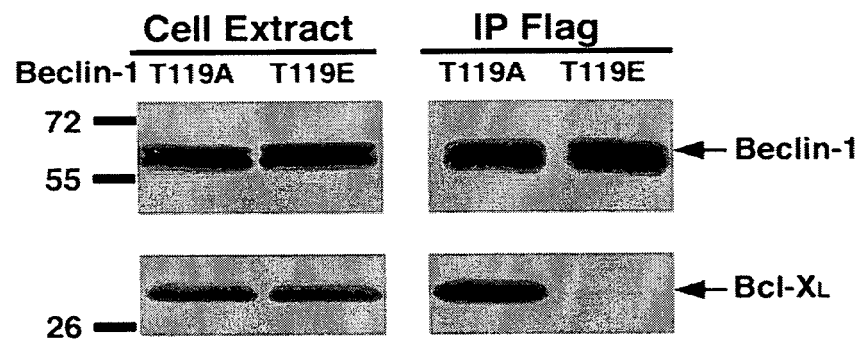
Figure 5D:
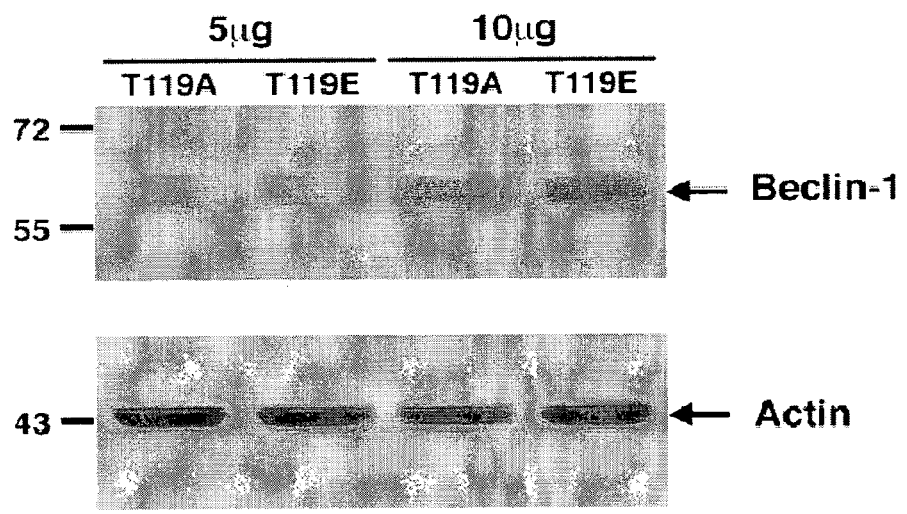
Figure 5E:
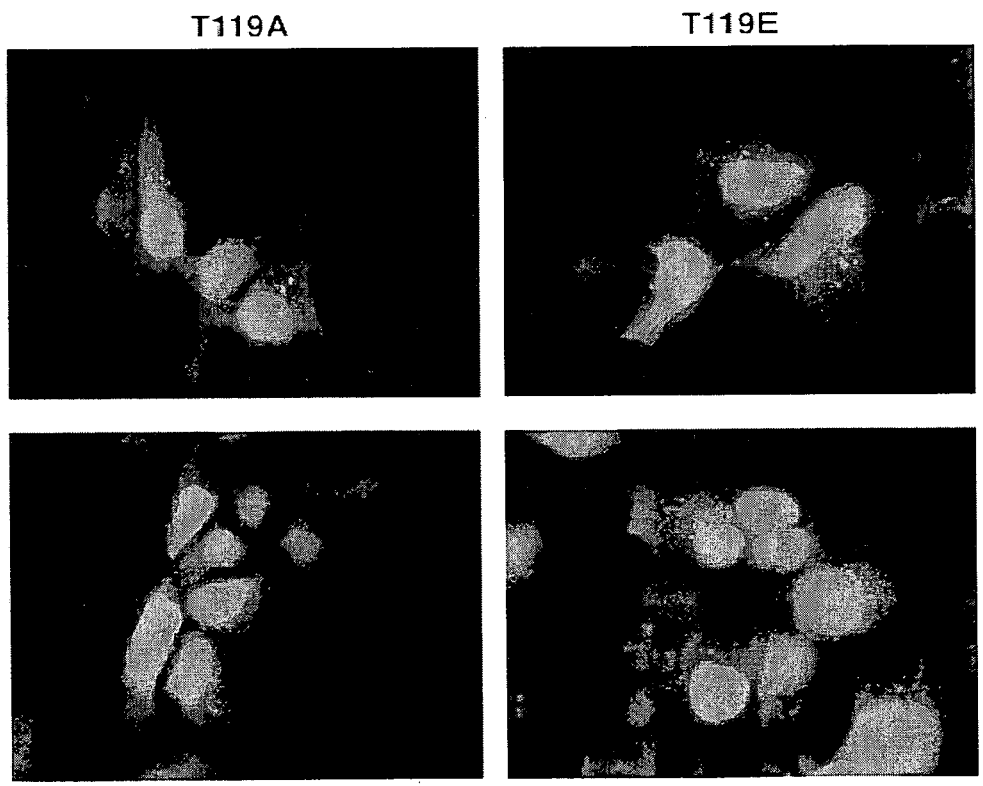
Figure 5F:
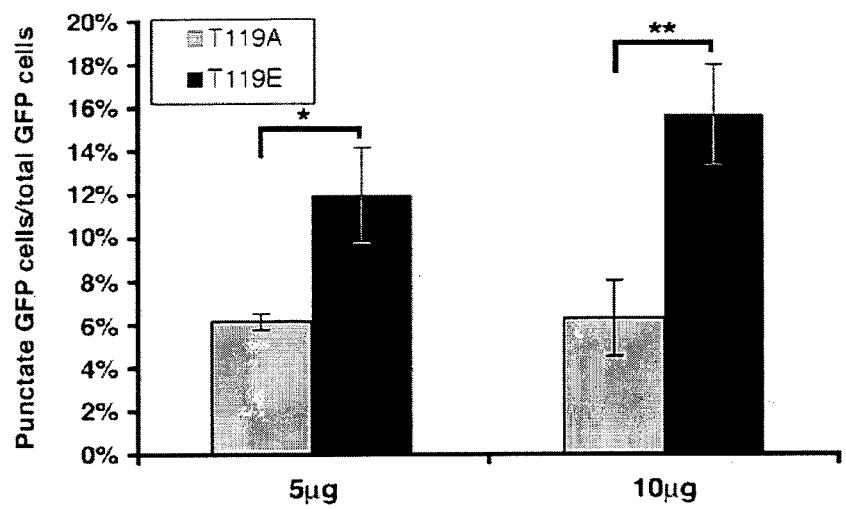
Figure 5G:
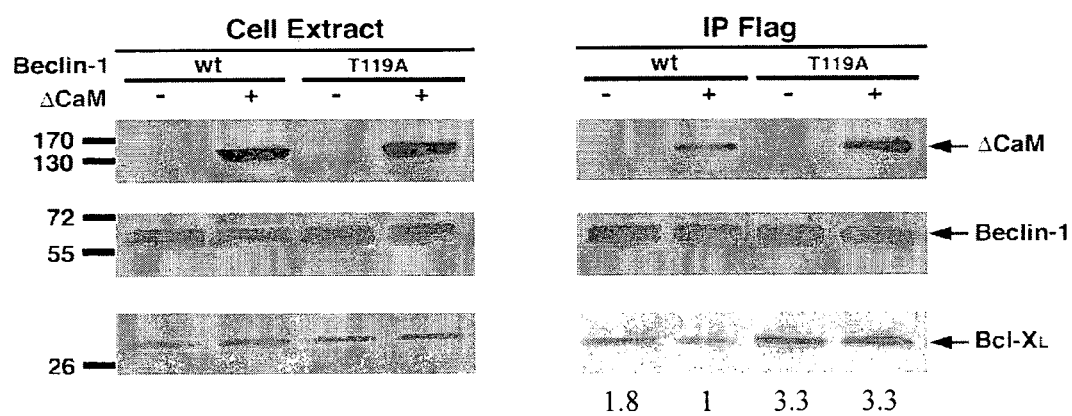

To examine the influence of DAPk on Beclin's interaction with Bcl-$X_L$, HEK293 cells were co-transfected with Bcl-$X_L$ and Flag-tagged Beclin-1 with or without HA-tagged (hemagglutinin epitope YPYDVPDYA (SEQ ID NO: 5)) DAPk. Beclin-1 was immunoprecipitated using anti-Flag antibodies, and the co-immunoprecipitated proteins as well as the total cell extracts were blotted using the indicated antibodies. It was found that the levels of Bcl-$X_L$ which co-immunoprecipitated with Beclin-1 were significantly reduced in the DAPk-transfected cells (FIG. 5A), suggesting that DAPk promotes Beclin's dissociation from Bcl-$X_L$. Similar results were obtained when cells were co-transfected with ΔCaM DAPk (FIG. 5B). To find out whether the phosphorylation at position Thr119 is causal to the reduced association of Beclin-1 with Bcl-$X_L$, a phospho-mimicking mutant of Beclin-1 (T119E) was generated, and tested its binding to Bcl-$X_L$ in these co-transfection assays as compared to the phospho-silencing mutation (T119A). It was found that the T to E substitution at position 119 strongly reduced the binding to Bcl-$X_L$ (FIG. 5C). In parallel the ability of these mutants to induce autophagy was compared using the GFP-LC3 punctate staining assay. HEK293 cells were transfected with 5 or 10 μg T119A or T119E Beclin-1 mutants together with GFP-LC3 plasmid. After 24 hours cells were counted and lysates were prepared. Western blot analysis was performed using the indicated antibodies. While the two mutants were expressed to the same extent (FIG. 5D), the frequency of cells in which the GFP-LC3 appeared in puncta increased in a dose dependent manner only when the Beclin-1 T119E mutant was introduced to the cells (FIGS. 5E-F). Together these results imply that phosphorylation on Thr119 is causing Beclin's dissociation from Bcl-$X_L$, leading to increased autophagosome formation. We also found that the suppressive effects of DAPk on Beclin-1's association with Bcl-$X_L$ shown in FIGS. 6A and 6B exclusively depended on Thr119 phosphorylation. HEK293 cells were transfected with Bcl-$X_L$, Flag-tagged Beclin-1 (wt) or Flag-tagged T119A Beclin-1 mutant with or without HA-tagged activated DAPk (ΔCaM). Beclin-1 was immunoprecipitated using anti-Flag antibodies, and the co-immunoprecipitated proteins as well as the total cell extracts were blotted. Bcl-$X_L$ levels were quantified using NIH image software, and the ratio between immunoprecipitated and the expressed Bcl-$X_L$ was calculated. As shown in FIG. 5G, ΔCaM DAPk had no effect on the amount of Bcl-$X_L$ which co-immunoprecipitated with the T119A Beclin-1 mutant while it reduced the amounts of Bcl-$X_L$ immunoprecipitated by the wt Beclin-1. Notably, DAPk was present in both Beclin-1 immunoprecipitates (FIG. 5+ΔCaM). Also, higher levels of Bcl-$X_L$ co-immunoprecipitated with T119A Beclin-1 than with wt Beclin-1 in the presence or absence of DAPk (FIG. 5G). Thus, lack of phosphorylation at position Thr119 leads to a stronger interaction between Beclin-1 and Bcl-$X_L$ which becomes resistant to DAPk dissociating effects. Transmission Electron Microscopy studies confirmed that under the specific conditions used in FIG. 5G (i.e., co-transfection of ΔCaM DAPk with wt Beclin-1 and Bcl-$X_L$) typical double membrane autophagosomes accumulated in cells thus confirming that autophagy was induced in these cellular settings (FIGS. 5H-K).

Example 6

DAPk Promotes Beclin's Dissociation from Bcl-2

Figure 6:
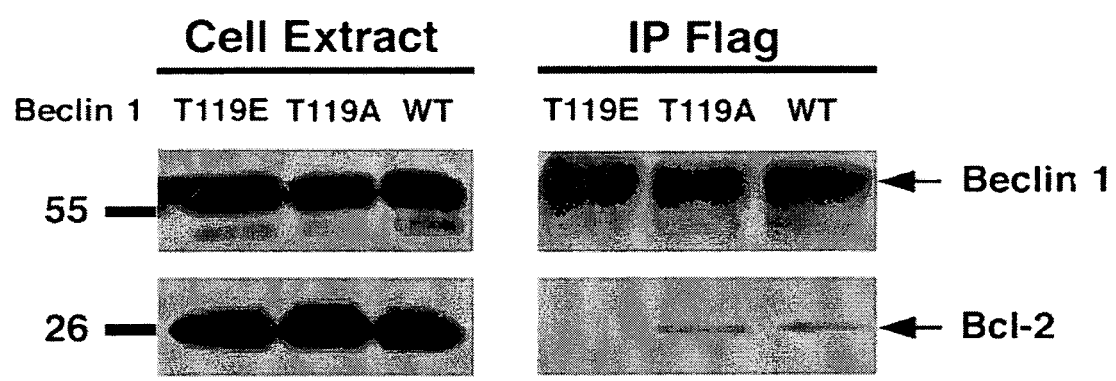
FIG. 6: Phosphorylation on Beclin-1's Thr119 reduces its interaction with Bcl-2.

To further investigate whether the Thr119 phosphorylation reduces association of Beclin-1 and Bcl-2, we used the phospho-mimicking (T119E) and the phosphor-silencing (T119A) mutants of Beclin-1 and tested their binding to Bcl-2, as compared to the wild-type Beclin-1. HEK293T cells were contransfected with Flag-tagged Beclin-1 and Bcl-2, and anti-Flag immunoprecipitates were immunoblotted with anti-Bcl-2 antibodies. The threonine to glutamic acid substitution at position 119 strongly reduced the binding of Beclin-1 to Bcl-2. These results suggest that phosphorylation on Thr119 also reduced the association of Beclin-1 with Bcl-2 (FIG. 6).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An isolated antibody or an antigen binding fragment thereof having specific binding affinity for a phosphorylated human Beclin-1 (SEQ ID NO: 1), wherein residue Thr 119 of the human Beclin-1 is phosphorylated (pThr 119) and the antibody recognizes a phosphorylated epitope comprising amino acids 115-123 (pThr 119) of the human Beclin-1 (SEQ ID NO: 1).

2. The antibody of claim 1, wherein the antibody is polyclonal.

3. The antibody of claim 1, wherein the antibody is monoclonal.

4. The antibody of claim 1, wherein the antibody recognizes a phosphorylated epitope consisting of amino acids 115-123 (pThr 119) of the human Beclin-1 (SEQ ID NO: 1).

5. The antibody of claim 1, wherein the antibody is generated with a synthetic phosphorylated peptide comprising amino acids 115-123 (pThr 119) of the human Beclin-1 (SEQ ID NO: 1).

6. The antibody of claim 1, wherein the antibody is generated with a synthetic phosphorylated peptide consisting of amino acids 115-123 (pThr 119) of the human Beclin-1 (SEQ ID NO: 1).

7. A kit for analyzing the level of human Beclin-1 that is phosphorylated at position Thr119 in a biological test sample, comprising the antibody of claim 1 and instructions for performing the analysis.

* * * * *

SEQUENCE LISTING

<160> NUMBER OF SEQ ID NOS: 5

<210> SEQ ID NO 1
<211> LENGTH: 450
<212> TYPE: PRT
<213> ORGANISM: Homo sapiens

<400> SEQUENCE: 1

```
Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
        35                  40                  45

Thr Ala Gln Ala Lys Pro Gly Glu Thr Gln Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
                85                  90                  95

Phe Thr Leu Ile Gly Glu Val Ser Asp Gly Gly Thr Met Glu Asn Leu
            100                 105                 110

Ser Arg Arg Leu Lys Val Thr Gly Asp Leu Phe Asp Ile Met Ser Gly
        115                 120                 125

Gln Thr Asp Val Asp His Pro Leu Cys Glu Glu Cys Thr Asp Thr Leu
    130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
                165                 170                 175

Ser Glu Gln Leu Gln Met Glu Leu Lys Glu Leu Ala Leu Glu Glu Glu
            180                 185                 190

Arg Leu Ile Gln Glu Leu Glu Asp Val Glu Lys Asn Arg Lys Ile Val
        195                 200                 205

Ala Glu Asn Leu Glu Lys Val Gln Ala Glu Ala Glu Arg Leu Asp Gln
    210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
                245                 250                 255

Ala Gln Thr Gln Leu Asp Lys Leu Lys Lys Thr Asn Val Phe Asn Ala
            260                 265                 270

Thr Phe His Ile Trp His Ser Gly Gln Phe Gly Thr Ile Asn Asn Phe
        275                 280                 285

Arg Leu Gly Arg Leu Pro Ser Val Pro Val Glu Trp Asn Glu Ile Asn
    290                 295                 300

Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
                325                 330                 335
```

```
Ser Tyr Leu Glu Ser Leu Thr Asp Lys Ser Lys Glu Leu Pro Leu Tyr
            340                 345                 350

Cys Ser Gly Gly Leu Arg Phe Phe Trp Asp Asn Lys Phe Asp His Ala
            355                 360                 365

Met Val Ala Phe Leu Asp Cys Val Gln Gln Phe Lys Glu Glu Val Glu
    370                 375                 380

Lys Gly Glu Thr Arg Phe Cys Leu Pro Tyr Arg Met Asp Val Glu Lys
385                 390                 395                 400

Gly Lys Ile Glu Asp Thr Gly Ser Gly Gly Ser Tyr Ser Ile Lys
            405                 410                 415

Thr Gln Phe Asn Ser Glu Glu Gln Trp Thr Lys Ala Leu Lys Phe Met
            420                 425                 430

Leu Thr Asn Leu Lys Trp Gly Leu Ala Trp Val Ser Ser Gln Phe Tyr
            435                 440                 445

Asn Lys
    450

<210> SEQ ID NO 2
<211> LENGTH: 450
<212> TYPE: PRT
<213> ORGANISM: Artificial Sequence
<220> FEATURE:
<223> OTHER INFORMATION: A recombinant homo sapiens Beclin-1 protein in
      which the Threonine residue at position 119 was replaced by a
      Glutamic acid reside (T119E)

<400> SEQUENCE: 2

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
            35                  40                  45

Thr Ala Gln Ala Lys Pro Gly Glu Thr Gln Glu Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
            85                  90                  95

Phe Thr Leu Ile Gly Glu Val Ser Asp Gly Gly Thr Met Glu Asn Leu
            100                 105                 110

Ser Arg Arg Leu Lys Val Glu Gly Asp Leu Phe Asp Ile Met Ser Gly
            115                 120                 125

Gln Thr Asp Val Asp His Pro Leu Cys Glu Glu Cys Thr Asp Thr Leu
    130                 135                 140

Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
            165                 170                 175

Ser Glu Gln Leu Gln Met Glu Leu Lys Glu Leu Ala Leu Glu Glu Glu
            180                 185                 190

Arg Leu Ile Gln Glu Leu Glu Asp Val Glu Lys Asn Arg Lys Ile Val
            195                 200                 205

Ala Glu Asn Leu Glu Lys Val Gln Ala Glu Ala Glu Arg Leu Asp Gln
    210                 215                 220

Glu Glu Ala Gln Tyr Gln Arg Glu Tyr Ser Glu Phe Lys Arg Gln Gln
225                 230                 235                 240
```

-continued

```
Leu Glu Leu Asp Asp Glu Leu Lys Ser Val Glu Asn Gln Met Arg Tyr
            245                 250                 255

Ala Gln Thr Gln Leu Asp Lys Leu Lys Lys Thr Asn Val Phe Asn Ala
            260                 265                 270

Thr Phe His Ile Trp His Ser Gly Gln Phe Gly Thr Ile Asn Asn Phe
            275                 280                 285

Arg Leu Gly Arg Leu Pro Ser Val Pro Val Glu Trp Asn Glu Ile Asn
            290                 295                 300

Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
            325                 330                 335

Ser Tyr Leu Glu Ser Leu Thr Asp Lys Ser Lys Glu Leu Pro Leu Tyr
            340                 345                 350

Cys Ser Gly Gly Leu Arg Phe Phe Trp Asp Asn Lys Phe Asp His Ala
            355                 360                 365

Met Val Ala Phe Leu Asp Cys Val Gln Gln Phe Lys Glu Glu Val Glu
            370                 375                 380

Lys Gly Glu Thr Arg Phe Cys Leu Pro Tyr Arg Met Asp Val Glu Lys
385                 390                 395                 400

Gly Lys Ile Glu Asp Thr Gly Ser Gly Ser Tyr Ser Ile Lys
            405                 410                 415

Thr Gln Phe Asn Ser Glu Gln Trp Thr Lys Ala Leu Lys Phe Met
            420                 425                 430

Leu Thr Asn Leu Lys Trp Gly Leu Ala Trp Val Ser Ser Gln Phe Tyr
            435                 440                 445

Asn Lys
   450
```

<210> SEQ ID NO 3
<211> LENGTH: 450
<212> TYPE: PRT
<213> ORGANISM: Artificial Sequence
<220> FEATURE:
<223> OTHER INFORMATION: A recombinant homo sapiens Beclin-1 protein in
      which the Threonine residue at position 119 was replaced by an
      Aspartic acid reside (T119D)

<400> SEQUENCE: 3

```
Met Glu Gly Ser Lys Thr Ser Asn Asn Ser Thr Met Gln Val Ser Phe
1                   5                  10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
            35                  40                  45

Thr Ala Gln Ala Lys Pro Gly Glu Thr Gln Glu Glu Glu Thr Asn Ser
    50                  55                  60

Gly Glu Glu Pro Phe Ile Glu Thr Pro Arg Gln Asp Gly Val Ser Arg
65                  70                  75                  80

Arg Phe Ile Pro Pro Ala Arg Met Met Ser Thr Glu Ser Ala Asn Ser
            85                  90                  95

Phe Thr Leu Ile Gly Glu Val Ser Asp Gly Gly Thr Met Glu Asn Leu
            100                 105                 110

Ser Arg Arg Leu Lys Val Asp Gly Asp Leu Phe Asp Ile Met Ser Gly
            115                 120                 125

Gln Thr Asp Val Asp His Pro Leu Cys Glu Glu Cys Thr Asp Thr Leu
    130                 135                 140
```

```
Leu Asp Gln Leu Asp Thr Gln Leu Asn Val Thr Glu Asn Glu Cys Gln
145                 150                 155                 160

Asn Tyr Lys Arg Cys Leu Glu Ile Leu Glu Gln Met Asn Glu Asp Asp
            165                 170                 175

Ser Glu Gln Leu Gln Met Glu Leu Lys Glu Leu Ala Leu Glu Glu Glu
        180                 185                 190

Arg Leu Ile Gln Glu Leu Glu Asp Val Glu Lys Asn Arg Lys Ile Val
    195                 200                 205

Ala Glu Asn Leu Glu Lys Val Gln Ala Glu Ala Glu Arg Leu Asp Gln
210                 215                 220

Glu Glu Ala Gln Tyr Gln Arg Glu Tyr Ser Glu Phe Lys Arg Gln Gln
225                 230                 235                 240

Leu Glu Leu Asp Asp Glu Leu Lys Ser Val Glu Asn Gln Met Arg Tyr
            245                 250                 255

Ala Gln Thr Gln Leu Asp Lys Leu Lys Lys Thr Asn Val Phe Asn Ala
        260                 265                 270

Thr Phe His Ile Trp His Ser Gly Gln Phe Gly Thr Ile Asn Asn Phe
    275                 280                 285

Arg Leu Gly Arg Leu Pro Ser Val Pro Val Glu Trp Asn Glu Ile Asn
290                 295                 300

Ala Ala Trp Gly Gln Thr Val Leu Leu Leu His Ala Leu Ala Asn Lys
305                 310                 315                 320

Met Gly Leu Lys Phe Gln Arg Tyr Arg Leu Val Pro Tyr Gly Asn His
            325                 330                 335

Ser Tyr Leu Glu Ser Leu Thr Asp Lys Ser Lys Glu Leu Pro Leu Tyr
        340                 345                 350

Cys Ser Gly Gly Leu Arg Phe Phe Trp Asp Asn Lys Phe Asp His Ala
    355                 360                 365

Met Val Ala Phe Leu Asp Cys Val Gln Gln Phe Lys Glu Glu Val Glu
370                 375                 380

Lys Gly Glu Thr Arg Phe Cys Leu Pro Tyr Arg Met Asp Val Glu Lys
385                 390                 395                 400

Gly Lys Ile Glu Asp Thr Gly Ser Gly Ser Tyr Ser Ile Lys
            405                 410                 415

Thr Gln Phe Asn Ser Glu Glu Leu Trp Thr Lys Ala Leu Lys Phe Met
        420                 425                 430

Leu Thr Asn Leu Lys Trp Gly Leu Ala Trp Val Ser Ser Gln Phe Tyr
            435                 440                 445

Asn Lys
    450

<210> SEQ ID NO 4
<211> LENGTH: 450
<212> TYPE: PRT
<213> ORGANISM: Artificial Sequence
<220> FEATURE:
<223> OTHER INFORMATION: A recombinant homo sapiens Beclin-1 protein in
      which the Threonine residue at position 119 was replaced by an
      Alanine reside (T119A)

<400> SEQUENCE: 4

Met Glu Gly Ser Lys Thr Ser Asn Asn Ser Thr Met Gln Val Ser Phe
1               5                   10                  15

Val Cys Gln Arg Cys Ser Gln Pro Leu Lys Leu Asp Thr Ser Phe Lys
            20                  25                  30

Ile Leu Asp Arg Val Thr Ile Gln Glu Leu Thr Ala Pro Leu Leu Thr
        35                  40                  45
```

-continued

Thr Ala Gln Ala Lys Pro Gly Glu Thr Gln Glu Glu Thr Asn Ser
 50              55              60

Gly Glu Glu Pro Phe Ile Glu Thr Pro Arg Gln Asp Gly Val Ser Arg
 65                  70              75              80

Arg Phe Ile Pro Pro Ala Arg Met Met Ser Thr Glu Ser Ala Asn Ser
             85              90              95

Phe Thr Leu Ile Gly Glu Val Ser Asp Gly Thr Met Glu Asn Leu
             100             105             110

Ser Arg Arg Leu Lys Val Ala Gly Asp Leu Phe Asp Ile Met Ser Gly
         115             120             125

Gln Thr Asp Val Asp His Pro Leu Cys Glu Glu Cys Thr Asp Thr Leu
 130             135             140

Leu Asp Gln Leu Asp Thr Gln Leu Asn Val Thr Glu Asn Glu Cys Gln
145             150             155             160

Asn Tyr Lys Arg Cys Leu Glu Ile Leu Glu Gln Met Asn Glu Asp Asp
             165             170             175

Ser Glu Gln Leu Gln Met Glu Leu Lys Glu Leu Ala Leu Glu Glu Glu
         180             185             190

Arg Leu Ile Gln Glu Leu Glu Asp Val Glu Lys Asn Arg Lys Ile Val
         195             200             205

Ala Glu Asn Leu Glu Lys Val Gln Ala Glu Ala Glu Arg Leu Asp Gln
 210             215             220

Glu Glu Ala Gln Tyr Gln Arg Glu Tyr Ser Phe Lys Arg Gln Gln
225             230             235             240

Leu Glu Leu Asp Asp Glu Leu Lys Ser Val Glu Asn Gln Met Arg Tyr
             245             250             255

Ala Gln Thr Gln Leu Asp Lys Leu Lys Lys Thr Asn Val Phe Asn Ala
         260             265             270

Thr Phe His Ile Trp His Ser Gly Gln Phe Gly Thr Ile Asn Asn Phe
         275             280             285

Arg Leu Gly Arg Leu Pro Ser Val Pro Val Glu Trp Asn Glu Ile Asn
 290             295             300

Ala Ala Trp Gly Gln Thr Val Leu Leu Leu His Ala Leu Ala Asn Lys
305             310             315             320

Met Gly Leu Lys Phe Gln Arg Tyr Arg Leu Val Pro Tyr Gly Asn His
             325             330             335

Ser Tyr Leu Glu Ser Leu Thr Asp Lys Ser Lys Glu Leu Pro Leu Tyr
         340             345             350

Cys Ser Gly Gly Leu Arg Phe Phe Trp Asp Asn Lys Phe Asp His Ala
         355             360             365

Met Val Ala Phe Leu Asp Cys Val Gln Gln Phe Lys Glu Glu Val Glu
 370             375             380

Lys Gly Glu Thr Arg Phe Cys Leu Pro Tyr Arg Met Asp Val Glu Lys
385             390             395             400

Gly Lys Ile Glu Asp Thr Gly Ser Gly Ser Tyr Ser Ile Lys
             405             410             415

Thr Gln Phe Asn Ser Glu Glu Trp Thr Lys Ala Leu Lys Phe Met
         420             425             430

Leu Thr Asn Leu Lys Trp Gly Leu Ala Trp Val Ser Ser Gln Phe Tyr
         435             440             445

Asn Lys
 450

```
<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Tyr Pro Tyr Asp Val Pro Asp Tyr Ala
1               5
```